US012371633B2

(12) United States Patent
Chandrasekaran et al.

(10) Patent No.: US 12,371,633 B2
(45) Date of Patent: Jul. 29, 2025

(54) COLD TREATMENT

(71) Applicant: SYMRISE AG, Holzminden (DE)

(72) Inventors: Vijayanand Chandrasekaran, Holzminden (DE); Stefan Brennecke, Halle (DE); Uwe Schaar, Holzminden (DE); Edison Diaz Gomez, Goslar (DE); Claudia Utermöhle, Uslar (DE); Pierre Kurzenne, Bois-Colombes (FR)

(73) Assignee: SYMRISE AG, Holzminden (DE)

( * ) Notice: Subject to any disclaimer, the term of this patent is extended or adjusted under 35 U.S.C. 154(b) by 1237 days.

(21) Appl. No.: 16/635,680

(22) PCT Filed: Aug. 1, 2017

(86) PCT No.: PCT/EP2017/069404
§ 371 (c)(1),
(2) Date: Jan. 31, 2020

(87) PCT Pub. No.: WO2019/024983
PCT Pub. Date: Feb. 7, 2019

(65) Prior Publication Data
US 2021/0122995 A1   Apr. 29, 2021

(51) Int. Cl.
*C11B 9/02*    (2006.01)
*A23L 5/40*    (2016.01)
(Continued)

(52) U.S. Cl.
CPC .............. *C11B 9/022* (2013.01); *A23L 5/40* (2016.08); *A23L 27/13* (2016.08); *A61K 8/922* (2013.01);
(Continued)

(58) Field of Classification Search
None
See application file for complete search history.

(56) References Cited

U.S. PATENT DOCUMENTS

| 9,539,549 B2 * | 1/2017 | Haensel | B01D 67/009 |
| 10,202,562 B2 | 2/2019 | Boam et al. | |
| 2002/0160066 A1 * | 10/2002 | Majeed | A61K 8/35 514/765 |

FOREIGN PATENT DOCUMENTS

| CN | 104302384 A | 1/2015 |
| CN | 106148013 A | 11/2016 |

(Continued)

OTHER PUBLICATIONS

Machine translation of DE 102009047351 (pp. 1-10). (Year: 2011).*
(Continued)

*Primary Examiner* — Clare M Perrin
(74) *Attorney, Agent, or Firm* — MARSHALL, GERSTEIN & BORUN LLP

(57) ABSTRACT

The present invention relates to a new high-throughput process for reducing impurities in essential oils and extracts (in particular for fragrances, fragrance ingredients, flavours and cosmetic ingredients) under mild conditions. Undesirable natural components such as waxes, but also synthetic materials such as agrochemicals and other environmental pollutants are reduced by using at least one selective nano-filtration membrane. In addition, the present invention relates to a method for reducing coloured components in essential oils to obtain a less coloured or even colourless essential oil, while achieving high re-colouration stability over time. Further, the odour quality is maintained or increased through reduction of undesirable olfactory substances to achieve a purified and higher quality oil.

14 Claims, 8 Drawing Sheets

(51) Int. Cl.
  *A23L 27/12* (2016.01)
  *A61K 8/92* (2006.01)
  *A61Q 13/00* (2006.01)
  *A61Q 19/10* (2006.01)
  *B01D 61/02* (2006.01)
  *B01D 69/02* (2006.01)
  *B01D 69/10* (2006.01)
  *B01D 69/12* (2006.01)
  *B01D 71/70* (2006.01)

(52) U.S. Cl.
  CPC .............. *A61Q 13/00* (2013.01); *A61Q 19/10* (2013.01); *B01D 61/027* (2013.01); *B01D 69/02* (2013.01); *B01D 69/107* (2022.08); *B01D 69/1218* (2022.08); *B01D 71/701* (2022.08); *A23V 2002/00* (2013.01); *A61K 2800/5922* (2013.01); *B01D 2325/20* (2013.01)

(56) References Cited

FOREIGN PATENT DOCUMENTS

| | | | | |
|---|---|---|---|---|
| DE | 44 21 682 A1 | 2/1995 | | |
| DE | 102009047351 A1 * | 6/2011 | ........... | B01D 67/009 |
| EP | 2205710 A1 * | 7/2010 | ........... | A23L 1/2225 |
| JP | S61-222508 A | 10/1986 | | |
| JP | 2015-521219 A | 7/2015 | | |
| PH | 12015502810 B1 | 3/2016 | | |
| WO | WO-2013167307 A1 * | 11/2013 | ........... | B01D 61/027 |
| WO | WO-2014/203581 A1 | 12/2014 | | |

OTHER PUBLICATIONS

Werhan et al. (Journal of Membrane Science, 2012, 423-424, 404-412). (Year: 2012).*
International Search Report and Written Opinion from International Application No. PCT/EP2017/069404 dated Oct. 11, 2017.
Notice of Reasons for Refusal for Japanese Application No. 2020-505445, dated Mar. 31, 2021.
Office Action (and English translation) from Chinese Application No. 201780093531.1 dated Aug. 11, 2022.
Schaepertoens et al., "Solvent recycle with imperfect membranes: A semi-continuous workaround for diafiltration," Journal of Membrane Science 514:646-658 (2016).

* cited by examiner

COLD TREATMENT

CROSS-REFERENCE TO RELATED APPLICATIONS

This is a U.S. National Phase of International Application No. PCT/EP2017/069404, filed Aug. 1, 2017.

The present invention discloses a new high-throughput process for reducing impurities in essential oils and extracts (in particular for fragrances, fragrance ingredients, flavours and cosmetic ingredients) under mild conditions. Undesirable natural components such as waxes, but also synthetic materials such as agrochemicals and other environmental pollutants are reduced by using at least one selective nanofiltration membrane. In addition, the present invention relates to a method for reducing coloured components in essential oils to obtain a less coloured or even colourless essential oil, while achieving high re-colouration stability over time. Further, the odour quality is maintained or increased through reduction of undesirable olfactory substances to achieve a purified and higher quality oil.

Essential oils are used for example in the food and beverage industry as well as the flavour, cosmetic ingredient and fragrance industry. They also can have bactericidal, virucidal, fungicidal, antiparasitical, insecticidal, medicinal and cosmetic applications.

As these impurities constitute a wide range of chemical species, the operations for removing the impurities include the use of adsorbents, distillation or washing the oil with various aqueous chemical solutions. However, the effectiveness of these operations is limited and may reduce the yield of the essential oil. In addition, achieving high selectivity in purification can lead to a decrease in operation speed. On an industrial scale, production efficiency must be ensured at the same time as product quality.

The use of membranes to concentrate the essential oil from an aqueous or organic solvent system is known. This separation generates an aqueous permeate and the essential oil is concentrated as a second phase in the retentate.

In EP 2 205 710 a membrane-based process (micro- or ultrafiltration) is described to remove wax compounds from citrus oils at 10° C.

The document WO 2013/167307 shows a polyimide containing nanomembrane-based process for reducing impurities or fractionating natural components.

The unwanted materials are often difficult to separate from the desired compounds and multi-step, energy-consuming processes are required to generate the desired products. Furthermore, the most valuable compounds in the essential oil are regularly thermally sensitive and it is a challenge to isolate these compounds at high yield without incurring thermal damage.

There, thus, remains a need in the art for a more efficient process for removing impurities from essential oils used as fragrances, fragrance ingredients and flavours.

The problem of the present invention was, therefore, to provide a process for refining essential oils by reduction of the coloured components. Also, the process should lead to essential oils with reduced colouring, that also show a reduction in re-colouration as occurs, e.g. due to light or oxidation on standing for a longer period of time.

Another problem of the present invention was to provide a process for refining essential oils, which maintains or increases the odour quality of the product. These effects should be achieved coincidentally with a high production output.

A special problem of the present invention was to provide a process which may achieve the combined effect of one or more of the conventional processing steps applied to essential oils (for instance colour removal (adsorption) and/or fetor removal) and/or pesticides removal in a single process and at the same time to ensure sufficiently high capacities (flow rates). The disclosed process should therefore simplify and/or speed up the production of an essential oil and improve oil yield and quality.

Another problem was to provide a process to purify essential oils, in particular fragrances, fragrance ingredients, flavours or cosmetic ingredients, in a more economical way, from impurities which have a molecular weight in the same dimension, i.e. 130 to 300 Da, while avoiding possible negative effects on the fragrance, flavour or cosmetic ingredient profile of the essential oil product. In addition, high molecular weight components such as waxes or furocumarin derivatives should be selectively removed.

As indicated above, the present invention sets out to provide a process that can be used on an industrial scale with sufficient flux. Thus, the production process should also save energy and costs.

The problems of the present invention are solved by a process according to claim 1. Preferred embodiments are provided in the dependent claims and subsequent description.

In particular, the present disclosure relates to a process for removing coloured impurities, and/or maintaining or increasing the odour quality of the essential oil by reducing undesirable materials such as agrochemicals, fungicides or pesticides and other environmental pollutants such as iron, by:

(a) providing the essential oil and optionally mixing the essential oil with an organic solvent to form a solution;

(b) contacting the essential oil or the solution with at least one selective nanofiltration membrane, wherein a retentate is formed comprising at least one compound from the essential oil and a permeate is formed comprising at least one compound from the essential oil such that the compositions of the retentate and permeate solutions are different; and (c) optionally removing the organic solvent from the retentate to form a purified oil.

More specifically, this process removes coloured components which increase the lightness and chromaticity of the essential oil.

Therefore, in a first aspect, the invention relates to a nanofiltration process to provide a less coloured essential oil for a fragrance, flavour or cosmetic ingredient, comprising the following steps:

(i) providing a selectively permeable thin film composite (TFC) nanofiltration membrane, wherein the membrane consists of a support layer and a top layer, (ii) providing a flowable input, optionally with a solvent component;

(iii) separating the flowable input by transferring it across the surface of the membrane to form a retentate and a permeate, such that the concentration of one or more components of the permeate is reduced compared to the flowable input; and wherein the permeate is decoloured in comparison to the flowable input, such that the lightness value $L^*$ of the permeate is increased in comparison to the flowable input to $\Delta L^*$ greater than or equal to 1 and the chromaticity $C^*$ of the permeate is decreased in comparison to the flowable input to $\Delta C^*$ less than or equal to −2, according to the CIELAB colour measurement system, as specified by the International Commission on Illumination.

The term CIE L*a*b* (or CIELAB) is a colour space specified by the International Commission on Illumination (Commission internationale de l'éclairage, hence its CIE abbreviation). It describes mathematically all the colours visible to the human eye and was created to serve as a device-independent model to be used as a reference. This means that the colours are defined independent of their nature of creation or the device they are displayed on. It is the most general colour space for measuring colour within industry.

The three coordinates of CIELAB represent the lightness of the colour (L*=0 yields black and L*=100 indicates diffuse white; specular white may be higher), its position between red/magenta and green (a*, negative values indicate green, while positive values indicate magenta) and its position between yellow and blue (b*, negative values indicate blue and positive values indicate yellow). The space is mapped onto a three-dimensional integer space for device-independent digital representation, and for these reasons, the L*, a*, and b*values are absolute. Colours with no chroma always have the value a*=b*=0.

In the present case, the colour of the samples is measured by both lightness and chroma values; L* displays the brightness or darkness of the colour. The chromaticity, or colour saturation, distinguishes colour intensity or clarity (i.e. vividness vs. dullness) It is the vector distance from the colour centre.

The lower the chromaticity of the colour, the closer the colour is to so-called colourlessness. For the CIELAB system, C*=square root (a*square+b*square). The variegation of colours (chromaticity) C* in the CIELAB system is thus defined by:

$$C^* = \sqrt{a^2 + b^2}$$

whereby a* and b* are the colour coordinates in this system.

For the present invention, the lightness value L* of the permeate is increased in comparison to the flowable input to ΔL* greater than or equal to 1.

$$\Delta L^* = L^*(\text{permeate}) - L^*(\text{flowable input})$$

More preferably the increase in lightness is such that ΔL* greater than or equal to 2, even more preferably greater than or equal to 5.

In addition, the invention is characterised by a decrease in colourfulness/chromaticity in the filtered essential oils or their filtered solutions.

At the same time, the chromaticity of the filtered essential oils or their filtered solutions decreases.

$$\Delta C^* = C^*(\text{permeate}) - C^*(\text{flowable input})$$

Consequently, the chromaticity C* of the permeate is decreased in comparison to the flowable input and the value of ΔC* is less than or equal to -2, according to the CIELAB colour measurement system, as specified by the International Commission on Illumination. Preferably, for the above comparison, ΔC* is less than or equal to -3, and even more preferably less than or equal to -15. It was also possible to reduce the chromaticity by -20 or less.

Particularly preferred is that the decrease in chromaticity is achieved alongside the increase in lightness as described above.

In a second aspect of the invention, the lightness value L* of the permeate is increased in comparison to the flowable input to ΔL* greater than or equal to 1.5, preferably greater than or equal to 2.0, and/or the chromaticity C* of the permeate is decreased in comparison to the flowable input to ΔC* less than or equal to -4, preferably less than or equal to -10.

Typically, the retentate suffers an accumulation of unwanted coloured compounds or other by-products and higher molecular components such as waxes. Consequently, as regards the chromaticity and lightness of the retentate, there is an opposite decrease in lightness and increase in chromaticity as compared to the flowable input.

Furthermore, the inventive process is also characterised in that the transparency of the essential oils or their filtered solutions increases as compared to the flowable input or the retentate.

Although the chromaticity decreases in general towards the white-grey middle point in the CIELAB topography, there can also be a colour shift in colour space, preferably towards a more yellow product, in particular if this is accompanied by an increase in lightness. This is sometimes perceived as a generally lighter coloured product. Therefore, preferably b* is shifted to less positive values, which indicate a decrease in the yellow component. This is particularly noticeable in Citrus Oils such as Tangarine Oil. Preferably the shift in b* is greater than or equal to -20, more preferably greater or equal to -50. Even more preferably, the reduction in colour and increase in lightness are achieved at the same time as a decrease in yellow colour component.

These effects in reducing colour and increasing lightness are achieved and at the same time as maintaining or increasing production output. The process of the present invention combines the effects of one or more of the conventional processing steps applied to essential oils, for instance colour removal and/or fetor removal and/or pesticides removal, in a single process and at the same time. The disclosed process simplifies and speeds up the production of purified and colour-reduced essential oils and improves oil yield and quality. Therefore, the process to purify essential oils is more economical. These effects are achieved by the particular combination of the innovative process, the used organic solvents and the flow rate, according to the present invention.

The process of the present invention for refining essential oils with or without a solvent as described herein leads to a reduction of the coloured components. Also, further compounds, which lead to re-colouration with time by action of, e.g. light/UV or oxidation, were filtered out by the inventive process. Consequently, the process maintains or increases the odour quality of the product by refining essential oils.

Thus, in a third aspect of the invention, the colour stability of the permeate is such that the re-colouration measured by the change in lightness of the permeate a certain amount of time after nanofiltration in comparison to the permeate just after nanofiltration is increased or only decreased to ΔL* greater than or equal to -2.0, preferably greater than or equal to -1.0, more preferably greater than or equal to -0.5 and/or the chromaticity C* of the permeate a certain amount of time after nanofiltration is decreased or only increased in comparison to the permeate just after nanofiltration to ΔC* less than or equal to 10, preferably less than or equal to 5, most preferred less than or equal to 1.

The certain amount of time for maintaining the reduced colour stability is preferably at least 48 h, more preferably 20 days, even more preferably 21 weeks, most preferably 1 year. Alternatively, the certain amount of time can be at least 48 h of UV-light exposure, more preferably 1 week of UV-light exposure, most preferably 1 month of UV-light exposure. The above changes in lightness and chromaticity can be achieved during these time periods.

Thus, although re-colouration over time has been observed after nanofiltration treatment, it can be reduced considerably when employing the current inventive filtration technique.

These effects are achieved and simultaneously the production output is high. Therefore, the process to purify essential oils, in particular for fragrances, fragrance ingredients, flavours and cosmetic ingredients is more economical.

In a fourth preferred aspect of the invention, the TFC nanofiltration membrane does not include a nitrogen-containing polymer.

In general, membrane processes have been used for industrial applications and have provided alternatives for more traditional purification and separation processes (such as distillation, evaporation, adsorption, extraction, and chromatography). This has been motivated by the benefits that membrane technology offers over conventional techniques, in terms of economy, environment, and safety to develop new membranes. The materials for membranes available for nanofiltration are polymeric as well as ceramic and mixed matrix. The two main types of membranes are integrally skinned asymmetric (ISA) membranes and thin film composite (TFC) membranes. They are both polymeric membranes. In the present invention TFC membranes are used, which consist of a separating layer cast on top of a more porous chemically different sublayer.

According to this invention, in the thin film composite (TFC) membranes, the ultrathin separating layer is defined as "top layer" and the more porous chemically different sublayer is defined as "support layer". Both layers are membranes, which are very flexible and characterized by some freedom in their design for a specific application. Because of the characteristic layered structure of the membrane support layer and top layer, the chemistry and performance of the two layers can be independently optimized to maximize the overall membrane performance. The choice of the support layer is as important as the selection of the top layer.

The thin film composite nanofiltration membranes are typically prepared by interfacial polymerization or via dip coating. Therefore, the more porous support layer is coated with different compositions to form the top layer. Alternatively, thin film composite nanofiltration membranes are made via plasma polymerization of diamond-like carbon (DLC) nano-sheets as a top amorphous carbon layer on the support layer.

In the present invention, the thin film composite nanofiltration membranes are preferably prepared by coating of the support layer.

It was observed that thin film composite (TFC) nanofiltration membranes including non-nitrogen-containing polymers showed strong decolouration. One possible explanation could be that the present inventive process removes the micro element iron in the purified essential oil. Therefore, it is preferred for the present invention that the thin film composite nanofiltration membrane does not include a nitrogen-containing polymer.

According to this invention, the support layer is used as a porous support that can be independently optimized to maximize the overall membrane performance. The material chosen for the support layer comprises the most common solvent-stable polymers used as supports for TFC membranes.

In a fifth preferred aspect, the invention relates to a process wherein the support layer of the TFC nanofiltration membrane comprises a polymer, which includes one or more of the heteroatoms O, N, S, and/or halogen, and/or Si, more preferably a polymer including the heteroatom O and/or S.

It was observed that particularly these TFC nanofiltration membranes showed excellent pesticide removal in the permeate. Therefore, it is particularly preferred for the present invention that the thin film composite nanofiltration membrane comprises a polymer, which includes one or more of the heteroatoms O, N, S, and/or halogen and/or Si. The best effects were shown using polymers including the heteroatom O, or N. Although non-nitrogen containing membranes are preferred for particular goals, in achieving other advantages, membranes including heteroatoms, such as also nitrogen-containing polymers, are also preferred. Particularly preferred is the use of PAN Polyacrylnitril in the membrane composition.

It was found that pesticide removal can be effectively achieved using only a single membrane according to the invention, whereas in the state of the art multiple membranes with varying cut-off values must be employed for effective pesticide reduction on the same scale.

In a sixth particularly preferred aspect, the invention relates to a process, wherein the support layer comprises a material chosen from polymers with S, O or halogen-heteroatom and/or Si, such as polydimethylsiloxane, polyoctylmethylsiloxane, poly[1-(trimethylsilyl)-1-propyne], polytetrafluoroethylene, polysulfone, polyethersulfone, polyvinylidene fluoride and polyetheretherketone and mixtures thereof.

The inventors found that TFC nanofiltration membranes, in which the support layer membrane is formed of polymers such as polysulfone, polyethersulfone, or polyetheretherketone showed the best effects for removing impurities, which lead to the colouration of the essential oil.

Preferably, the support layer of the thin film composite nanofiltration membrane comprises a material chosen from polymers with at least one S or O-heteroatom, such as, in particular, polysulfone, polyethersulfone, and mixtures thereof.

In an alternative variant, the support layer of the thin film composite nanofiltration membrane comprises a material chosen from polymers without any heteroatom, such as polyethylene, polypropylene and mixtures thereof. These TFC nanofiltration membranes also showed good essential oil decolouration properties.

In another development of the invention, the support layer of the thin film composite nanofiltration membrane comprises a material chosen from inorganic materials like silicon carbide, zeolite, zirconium oxide, titanium oxide or aluminium oxide and mixtures thereof.

According to this invention, the top layer, which is used as an ultrathin "separating layer", can be independently optimized to maximize the overall membrane performance. The material chosen for the top layer comprises solvent-stable polymers.

In a seventh aspect, the invention relates to a process, wherein the top layer comprises a material chosen from the group consisting of: polydimethylsiloxane, polyoctylmethylsiloxane, poly[1-(trimethylsilyl)-1-propyne], poly(2,6-dimethyl-1,4-phenylene oxide), polyacrylacid, polymer of intrinsic microporosity (PIM-1), polystryrene-b-poly(ethylene oxide) diblockcopolymer, poly(sodiumstyrenesulfonate (PSS), or polyvinylsufate (PVS) and mixtures thereof.

The inventors found that TFC nanofiltration membranes, in which the top layer membrane is formed of polymers such as polydimethylsiloxane, polyoctylmethylsiloxane, poly[1-(trimethylsilyl)-1-propyne], poly(2,6-dimethyl-1,4-phenylene oxide), polyacrylacid, polymer of intrinsic microporosity (PIM-1), polystryrene-b-poly(ethylene oxide) diblockcopolymer, poly(sodiumstyrenesulfonate (PSS), or polyvinylsufate (PVS) and mixtures thereof showed good effects for removing synthetic impurities, such as pesticides or fungicides.

This is particularly the case when the top layer is a silicone coated organophilic layer, preferably cross-linked polydimethylsiloxane, as is demonstrated in an eighth aspect of the invention.

More preferred are silicone coated thin film composite nanofiltration membranes. Particularly preferred are cross-linked silicone coated thin film composite nanofiltration membranes. These TFC nanofiltration membranes showed very good effects for removing synthetic impurities, in particular fungicides such as pyraclostrobin or trifloxystrobin or pesticides and insecticides including pyrethroides, such as bifenthrin, cyfluthrin, and p,p-dicofol or benzoylureas, such as diflubenzuron or flufenoxuron.

In a further preferred variant of the invention, the performance of thin film composite nanofiltration membranes, especially the top layer, can be further enhanced by applying an appropriate post-treatment method. Several techniques, such as curing, grafting, plasma, UV, cross-linking by e.g. irradiation and chemical treatment are known in the art.

Further, the thin film composite nanofiltration membranes can consist of organic-inorganic polymer hybrids which allow tailoring new membranes combining properties of both inorganic and polymeric materials.

Suitable selective membranes for use according to the present disclosure include polymeric and ceramic membranes, as well as mixed polymeric/inorganic membranes.

The thin film composite nanofiltration membranes of the present invention showed a reduction of the coloured components in essential oils by selectively removing coloured components. Further to the reduction of the coloured components in the essential oils, some membranes in particular also showed reduced re-colouration by e.g. light or oxidation on standing for longer durations (e.g. at least 48 h). Possibly the combination of the top layer and support layer membrane leads to the double effect of decolouration of the essential oil and removing of other compounds, such as easily oxidised components.

The membrane performance is characterized by different parameters. One parameter is the membrane nominal molecular weight cutoff (MWCO). The term "MWCO" is defined as the smallest solute molecular weight for which the membrane has 90% rejection (R (%)≥90).

Another parameter to characterize the membrane performance is the rejection (or selectivity). The term "rejection" is defined by equation (a), where $C_P$ is the solute concentration in permeate, "permeate" being the liquid which has passed through the membrane, and $C_R$ is the solute concentration in the retentate (or feed), wherein the "retentate" is the liquid which has not passed through the membrane.

$$R = 100 * (1 - C_P : C_R) \qquad (a)$$

According to a ninth aspect of the inventive process, the thin film composite nanofiltration membrane has a molecular weight cut off between 150 g/mol and 1200 g/mol.

Preferably, the thin film composite nanofiltration membrane has a molecular weight cut-off ranging from 300 g/mol to 700 g/mol and particularly preferred from 350 g/mol to 600 g/mol.

In a further advantageous variant of the invention, the thin film composite nanofiltration membrane has two different layers with preferably two different molecular weight cut-offs, especially preferred is at least one layer having a molecular weight cut-off between 200 g/mol and 1200 g/mol.

Preferably, the thin film composite nanofiltration membrane has at least one selective membrane with a molecular weight cut-off ranging from 300 g/mol to 700 g/mol, more preferred from 400 g/mol to 600 g/mol.

In a special development of the invention, the two layers have different molecular weight cut-off values, wherein at least one layer has a molecular weight cut-off between 150 g/mol and 400 g/mol and the other layer has a molecular weight cut-off between 500 g/mol and 700 g/mol.

The inventors found that TFC nanofiltration membranes, in which the top layer membrane is formed of polymers, showed good effects for removing naturally occurring impurities including waxes, such as aliphatic hydrocarbons, alcohols, and related ketones, aldehydes, acids, diols, coumarins, furocoumarine, sterols, flavonoids, vitamins, plant sterols, lipophilic hormones and oxidation products.

In a tenth aspect, the invention provides a process, which comprises an essential oil and a solvent, wherein the solvent comprises at least 10 wt. % organic solvent component, and optionally water, and the organic solvent component has a dipole moment of at least $3*10^{-30}$ Cm. It is possible to reduce this amount, but at least some organic solvent is preferred to ensure a high throughput filtration performance.

The solvent system has the advantage of greatly increasing the flow rate through the membrane. Typically, solvent combinations of from 4 parts essential and 1 part solvent to 1 part essential oil and 1 part solvent are preferred. This boosts the flux, in particular to the extent that the yield in essential oil per time unit is increased, even taking the extra step of solvent removal into account. In some cases, it is imperative to use a solvent to filter the essential oil at all.

Nanofiltration is a membrane filtration-based method. Nanofiltration membranes have pore sizes from 1 to 10 nanometres, smaller than that used in microfiltration and ultrafiltration, but larger than that in reverse osmosis.

In the present invention, the high flow rates and good separation are achieved by employing a solvent together with the essential oil during filtration. It is possible to conduct the membrane filtration process without a solvent, but in order to achieve high throughput, the flowable input is best generated by adding a solvent to the essential oil. In particular, the solvent comprises at least 10 wt. % organic solvent component and optionally water. It was found that most essential oils transportation processes work best when the organic solvent component has a dipole moment value of at least $3*10^{-30}$ Cm, when transported through the membranes according to the invention.

The term "dipole moment" is defined as the separation of positive and negative electrical charges within a molecule, that is, a measure of the molecule's overall polarity. The electric field strength of the dipole is proportional to the magnitude of dipole moment. The SI units for electric dipole moment are Coulomb-meter (Cm). Values for solvent dipole moments can be derived according to the list of Christian Reichardt, *Solvents and Solvent Effects in Organic Chemistry*, Wiley-VCH Publishers, 3rd ed., 2003.

In a preferred variant of the invention, the flowable input comprises an essential oil and an organic solvent, wherein the solvent comprises at least 10 wt. % organic solvent component. The essential oil is mixed with an organic solvent to form a homogeneous solution of oil and solvent. The mixing may be achieved by any technique known to one skilled in the art, such as, for example, via static inline mixer, dynamic inline mixer, and/or mixing vessel containing a mechanical stirrer. Preferably, the solution may contain the essential oil in an amount ranging from 10 to 50 wt. % organic solvent component to essential oil, particularly preferred from 10 to 20 wt. % organic solvent component to essential oil. Water may be used preferably as a co-solvent, in which case the amounts refer to the organic solvent-water mixture.

One advantage of using a solvent is that the dead volume of the membrane system is reduced by mixing the essential oil with an organic solvent.

In a preferred eleventh aspect of the invention, the organic solvent used to prepare the flowable input has a dipole moment of at least $4*10^{-30}$ Cm. Particularly useful solvents in this context are diethyl ether, ethanol, isopropanol, ethyl acetate methylethyl-ketone, methyl-tert-butyl-ether, cyclohexanol, butylacetat and acetone.

Particularly preferred solvents are such with an ether moiety, such as diethyl ether and methyl-tert-butyl-ether (MTBE). Also useful solvents in this context are solvents with an alcohol moiety, such as ethanol, isopropanol and cyclohexanol, of which ethanol and methyl-tert-butyl-ether (MTBE) are the most preferred. Methanol is generally not used in processes to filter essential oils for flavours.

The positive effect of the organic solvents according to this invention is that the flow rate increases. In order to achieve high selectivity and good decolouration, despite the higher flow rates, it is preferred to employ the membranes according to the invention.

In a different variant, the process of the invention employs an organic solvent component, which has a dipole moment of at less than $2*10^{-30}$ Cm. This is preferably hexane.

In another further improvement and twelfth aspect of the invention, the solvent further comprises a second organic solvent component, which has a dipole moment of at less than $2*10^{-30}$ Cm, preferably, less than $1*10^{-30}$ Cm and most preferred $0*10^{-30}$ Cm, i.e. is entirely apolar. Of these solvents, preferably hexane or heptane were useful as second apolar co-solvents. The use of a co-solvent has an effect on the flowability of the flowable input. The best results were observed using hexane.

It is particularly preferred in all variants of the present invention that the organic solvent used to prepare the mixture of essential oil and organic solvent is chosen from methyl-tert-butyl-ether (MTBE), diethyl ether, methylethyl-ketone, ethanol, and mixtures thereof. Particularly preferred organic solvents are ethanol and water mixtures, wherein the main component is ethanol, such as 95 vol % ethanol to 5 vol % water. The most particularly preferred organic solvents are methyl-tert-butyl-ether (MTBE) or ethanol to achieve high selectivity for removing impurities, despite the higher flow rates. It appears that these solvents have the best interaction with the used inventive TFC nanofiltration membranes.

The solvents employed work well with the membranes according to the invention, especially the nitrogen-free membranes, as described herein. It can thereby be ensured that membrane components do not leach into the essential oils. This is especially important for flavours.

In a preferred variation of the invention, the nanofiltration process for the purification of essential oils further comprises a step of recycling the retentate by redirecting the retentate to flow again across the surface of the membrane to form a subsequent retentate and permeate.

The term "recycling of the retentate" as used in this specification means to bring the retentate back to the feed tank and then transferring the flow again across the surface of the same membrane to form a further subsequent retentate and permeate.

The process disclosed herein can be applied in multiple stages. By way of non-limiting example, a second stage further comprises: providing the retentate from a first filtration that has been carried out to reduce the concentration of an impurity; passing the first retentate solution back to the feed tank and then again across the same or preferably a different selective TFC nanofiltration membrane, wherein a second retentate and a second permeate are formed and wherein a further impurity reduction has been carried out. This process can be reiterated to further comprise passing permeate from the second filtration again above a selective TFC membrane, to generate a third retentate and a third permeate under increasing purification. The process can be repeated for a fourth and fifth passing. Depending on the desired purification and yield, usually two or three iterations are sufficient to retain industrial scale yields and time efficiency of the process. The use of different membrane types allows a double selection of impurities that cannot be removed by one membrane type only.

In an alternative further development of the invention, the retentate is collected. For some applications, stronger, selectively more concentrated fragrance compositions are employed. The accumulation of certain components in the fragrance leads to useful new component accumulations.

In a preferred variation of the invention, the nanofiltration process for the purification of essential oils comprises the further step of collecting the permeate gained from the first and/or subsequent membrane filtration cycles. Typically this includes a step of removing the solvent from the purified essential oil gained as permeate.

A further factor of the invention process is the flux, which is defined as the liquid volume flowing through the membrane per unit area and per unit time [kg/m$^2$*h]). To achieve production flux has been optimised.

In a preferred thirteenth aspect of the invention, the flow rate through the membrane is at least 8 kg of permeate/hour*size of the membrane in m$^2$. Preferably the flow rate through the membrane is at least 12 kg of permeate/hour*size of the membrane in m$^2$. More preferably, the flow rate through the membrane is at least 20 kg of permeate/hour*size of the membrane in m$^2$. Most preferably the flow rate through the membrane is at least 50 kg of permeate/hour*size of the membrane in m$^2$.

The stated flow rate was calculated according the following. The results measured in gram/minute were transformed to kilogram/hour*square meter. The surface of the flat sheet TFC nanofiltration membrane was 28 cm$^2$.

In general, a particularly good combination of features according to the invention relates to a nanofiltration process for the purification of essential oils comprising: (i) providing a selectively permeable thin film composite (TFC) nanofiltration membrane, wherein the membrane consists of a support layer and a top layer, (ii) providing a flowable input, which comprises an essential oil and a solvent, wherein the solvent comprises at least 10 wt. % organic solvent component and optionally water and the organic solvent component has a dipole moment of at least $3*10^{-30}$ Cm, (iii) separating the flowable input by transferring it across the surface of the membrane to form a retentate and a permeate, such that the concentration of one or more components of the permeate is reduced compared to the flowable input; and wherein, the flow rate through the first membrane is at least 8 kg [permeate]/h*m$^2$ [membrane]. Herein, preferably the effects described for decolouration and lightness of the essential oils are also achieved.

The specific flow rate of the inventive process showed that no filter cake is formed on the membrane since it is washed away. At the same time synthetic impurities are removed selectively by the TFC nanofiltration membrane. The process of the present invention can be used in an industrial scale which requires a sufficient flux. Therefore, this process saves energy and costs. Adapting the membrane and solvent parameters to achieve higher flux rates is important for up-scaling the production.

To perform separations on an industrial scale, efficient and economical packaging of large membrane areas is also required. This is done by packing the membranes in modules. Three main factors contribute to the successful fabrication of a membrane module: the selection of the membrane material, for its appropriate chemical, mechanical, and permeation properties; the fabrication of the material into a defect-free, robust membrane; and the packaging of the membrane into a compact, high-surface-area module.

In another variant, the thin film composite nanofiltration membranes have different modules, such as spiral wound, envelope-type, flat sheet or tubular modules.

Spiral wound modules are available in a range of standard diameters. This module uses flat sheets wrapped around a central tube. The membranes are glued along three edges over a permeate spacer to form 'leaves'. The permeate spacer supports the membrane and conducts permeate to the central permeate tube. Between each leaf, a mesh like feed spacer is inserted. The size of the spiral wound module is from 0.3 to 5 $m^2$.

Tubular modules have bundles of tubes with the active surface of the membrane on the inside. Flow through the tubes is normally turbulent, ensuring low concentration polarisation, but also increasing energy costs. The tubes can either be self-supporting or supported by insertion into perforated metal tubes. This module design is limited for nanofiltration by the pressure it can withstand before bursting, thus limiting the maximum flux possible. Inorganic membranes are usually used in tubular modules. The size of the tubular module is from 0.5 to 2 $m^2$.

Flat-sheet modules are flat disc membranes. The disc size of the flat sheet module is between 20 to 250 $cm^2$. They are made of ceramic or polymeric material.

Envelope modules look similar to an envelope or a hollow fibre membrane. The envelope-type module offers some advantages as compared to spiral wound modules; it has very short permeate distances, and it does not require the use of a feed spacer and a glue, which are sometimes not stable in certain solvents. It has some disadvantages as it operates at a maximum pressure of 40 bar and the membrane area covered by a spiral wound module of the same size is larger.

Preferably, the thin film composite nanofiltration membranes used for this invention are spiral wound or flat sheet modules.

According to the invention, the flowable input preferably should have a viscosity in the range of 0.2 to 25 mPa*s. Even more preferred, the flowable input has a viscosity in the range of 0.2 to 2 mPa*s.

In another variant of the invention, the flowable input has a density in the range of 0.5 to 1.2 kg/l. The density of the flowable input is adapted to the solvent employed and to the essential oil. Therefore, the combination of essential oil and organic solvent related to the density of the flowable input. Preferably, the flowable input has a density in the range of 0.8 to 1.2 kg/l. Particularly preferred is that the flowable input has a density in the range of 0.8 to 1.0 kg/l. The density and viscosity of the flowable input also have an effect on the flowability of the flowable input. The best results were observed using the above mentioned ranges.

Some essential oils are known to be vulnerable to thermal degradation. The method disclosed herein is performed effectively at mild temperature conditions. These conditions are not harmful to the thermally-sensitive components. Therefore, the thermally-sensitive components are not converted to different chemical species which reduce their yield and may also change the fragrance properties or flavor of the essential oil.

Thus, in a further preferred variant of the invention, the process is performed at a temperature ranging from 10° C. to 50° C. and/or with a trans-membrane pressure ranging from 10 bar to 50 bar. A more preferred temperature range for carrying out the invention is 20 to 35° C. Preferably, the filtration is carried out under pressure in the range of 10 to 40 bar. More preferably, the trans-membrane pressure ranges from 20 bar to 35 bar. According to the invention, preferably, the nanofiltration process is performed at a temperature ranging from 10° C. to 40° C. and with a trans-membrane pressure ranging from 20 bar to 35 bar.

The reduction of undesirable natural and synthetic impurities may be achieved through contacting the solvent-oil solution with a thin film nanofiltration membrane that retains the undesirable impurities, i.e., in the form of a retentate, and allows permeation of the desired essential oil compounds, i.e., in the form of permeate. In at least one development of the invention, the trans-membrane pressure ranges from 10 to 40 bar.

Preferably the trans-membrane pressure may range from 25 to 35 bar, particularly preferred at 30 bar. In combination with the above temperature ranges, the selectivity is optimised, without secondary effects, such as product degradation.

In a further preferred variant, the process is performed under nitrogen or helium or inert atmosphere. Using an inert atmosphere has three positive effects. The first effect is that compounds which are susceptible to oxidation are protected by the inert atmosphere. The second effect is that there is no back-flow of the flowable input to the TFC nanofiltration membrane during the filtration process and, therefore, air insertions are excluded from the process. Further the inert gas provides explosion protection, which can be a problem using flammable organic solvents.

Although the inventive process is optimised for essential oils in general, the choice of essential oil can also be significant.

According to a fourteenth aspect, the invention works well with the following essential oils derived from the genus Citrus: sweet orange, orange, lemon, lime, grapefruit, bergamot, key lime, pomelo, citron, mandarine, tangerine, bitter orange, blood orange and/or wherein the essential oil is selected from the group consisting of: peru balsam oil, benzoin siam oil, patchouli oil, rose oil, ylang ylang oil, clove leaves, lemon oil, oak moss absolute and vanilla extract.

Preferably, in a fifteenth aspect, the essential oil is chosen from the group consisting of: mandarine oil, peru balsam, tangerine oil, blood orange oil, patchouli oil, vanilla extract and benzoin siam oil.

Particularly for such citrus oils, the removal of colour components was effective. Moreover, a shift towards a lighter, less yellow colour could be observed in some cases, which could be the result of a particularly effective removal of yellow colour components.

The essential oil is derived e.g. from plants and is preferably an oil produced from berries, seeds, bark, wood, rhizome, leaves, resin, flowers, peel and root. In such cases, also the removal of higher molecular weight components and waxes is important and can be achieved by the present process.

The essential oil can also be selected from oils deriving from angpur, persian lime, clementine, yuzu, kaffir lime, ugli, allspice oil, juniper oil, cumin oil, cinnamon bark oil, camphor oil, rosewood oil, ginger oil, basil oil, eucalyptus oil, lemongrass oil, mastic absolute, myrtle oil, peppermint oil, rosemary oil, spearmint oil, tea tree oil, frankincense oil, chamomile oil, clove oil, jasmine oil, lavender oil sandalwood oil, wormwood oil and valerian oil. Other preferred essential oils are those derived from cinnamon leaves, clove leaves, vetiver and lavender.

In another variant the invention relates to a process, wherein the essential oil is an aldehyde or ketone, such as anisaldehyde, citral, hydroxycitronellal, Lilial®, methyl-nonylacetaldehyde, allylionone, verbenone, nootkatone, geranylacetone, α-amylcinnamic aldehyde, Georgywood™, hydroxycitronellal, Iso E Super®, Isoraldeine® (methylionone), Hedione®, maltol, methyl cedryl ketone and vanillin; and/or wherein the essential oil is an alcohol, such as preferably selected from the group consisting of: cis-3-hexenol, cinnamic alcohol, citronellol, Ebanol®, eugenol, farnesol, geraniol, menthol, nerol, rhodinol, Super Muguet™, linalool, phenylethyl alcohol, Sandalore®, terpineol, Timberol® and 1-(2,2,6-Trimethylcyclohexyl) hexan-3-ol; and/or wherein the essential oil is an ether or acetal, such as preferably selected from the group consisting of: Ambrox®, geranyl methyl ether, rose oxide or Spirambrene®; and/or wherein the essential oil is an ester of lactone, such as preferably selected from the group consisting of: benzyl acetate, cedryl acetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, cis-3-hexenyl isobutyrate, linalyl acetate and geranyl acetate; and/or wherein the essential oil is a macrocycle, such as preferably selected from the group consisting of: ambrettolide, ethylene brassylate or Exaltolide®; and/or wherein the essential oil is a heterocycle, preferably isobutylquinoline.

The disclosed process of the present invention can remove a wide range of natural and synthetic impurities. Thus, the thereby obtained essential oils are suitable e.g. as cosmetic ingredients, flavours or fragrances and fragrance ingredients in general.

In a preferred primary variant, the removal of coloured components results in an oil having improved but preferably reduced colour. Also the process preferably removes further components that are responsible for re-colouring of the essential oil after some time. The coloured components or the source components for re-colouration of the essential oil may be natural and synthetic impurities or oxidation products thereof.

In another preferred development of the invention, the removal of unwanted smells and tastes result in an oil having an improved organoleptic profile. The source of unwanted smells and tastes in the essential oil may be e.g. oxidation products of natural and synthetic impurities. The unwanted natural and synthetic impurities typically have different chemical structures, sometimes entirely so. However, their selective removal depends on a balance of properties in the filtration membranes employed and the solvents used.

The synthetic impurities removed selectively by the inventive process include agrochemicals and their residues, such as fungicides, pesticides, biocides or insecticides and their breakdown products.

The removed pesticides also include organochlorine pesticides such as lindane, endrin, dieldrin, aldrin, isodrin, heptachlor-exo-epoxide, heptachlor-endo-epoxide, trans-chlordane, cis-chlordane, oxy-chlordane, chlordane, heptachlor, endosulfan-1 and mirex.

Preferably the inventive process removes pesticides or insecticides including pyrethroides, such as bifenthrin, cyfluthrin, and p,p-dicofol or benzoylureas such as diflubenzuron and flufenoxuron.

Further pesticides removed are preferably organophosphorus pesticides such as chlorpyrifos, methidathion, phosmet, parathion, malathion, methyl parathion, diazinon, dichlorvos, fenitrothion tetrachlorvinphos, azinphos methyl and organonitrogen pesticides such as propargite.

On the other hand, the inventive process also successfully removed fungicides. Such fungicides include strobilurines, such as azoxystrobin, pyraclostrobin and trifloxystrobin.

Also naturally occurring impurities could be removed, including waxes, such as aliphatic hydrocarbons, alcohols, and related ketones, aldehydes, acids, diols, coumarins, furocoumarine, sterols, flavonoids, vitamins, plant sterols, lipohilic hormones and oxidation products.

Preferably the inventive process removes furocoumarine, such as oxypeucedanin, heraclenin, byak-angelicol and 8-geranyloxypsoralen.

The environmental pollutants expected to be preferably removed include non-biodegradable pollutants which cannot be decomposed by living organisms and therefore persist in the ecosphere for extremely long periods of time. They include plastics, metal, glass, some pesticides and herbicides, as well as radioactive isotopes.

Further it was found that naturally occurring impurities or environmental pollutants including heavy metals could be selectively reduced in permeate. This was particularly effective for iron (Fe). It is important to reduce metals which can be an oxidative degeneration source and can trigger long-term re-colouration of the product essential oil.

Preferred heavy metals reduced are cobalt (Co), copper (Cu), chromium (Cr), iron (Fe), magnesium (Mg), manganese (Mn), molybdenum (Mo), nickel (Ni), selenium (Se) and zinc (Zn). Their multiple industrial, domestic, agricultural, medical and technological applications have led to their wide distribution in the environment. Although heavy metals are naturally occurring elements that are found throughout the earth's crust, most environmental contamination and human exposure result from industrial production and use, and domestic and agricultural use of metals and metal-containing compounds. The reduction of these impurities is particularly important for cosmetics ingredients and flavours.

The present invention also discloses a process for reducing natural impurities (e.g. waxes, oxidation products, and colored components) and synthetic impurities (e.g. agrochemical residues, heavy metals) present in an essential oil by employing a TFC nanofiltration membrane, wherein the membrane consists of a support layer and a top layer and wherein the thin film composite nanofiltration membrane includes a polymer containing one or more of the heteroatoms 0, N or S, comprising the steps of: (i) providing an essential oil; (ii) providing a flowable input, which comprises an essential oil and a solvent, wherein the solvent comprises at least 10 wt. % organic solvent component and optionally water and the organic solvent component has a dipole moment of at least $3*10^{-30}$ Cm; (iii) separating the flowable input by transferring it across the surface of the membrane to form a retentate and a permeate, such that the concentration of one or more components of the permeate is reduced compared to the flowable input; and wherein, the flow rate through the first membrane is at least 8 kg [permeate]/h*m² [membrane]; and wherein the membrane is selectively permeable membrane such that the membrane rejection ($R_{impurities}$) of the impurities is greater than the rejection ($R_{Oil}$) of the oil species.

The present disclosure also relates to compositions resulting from the process disclosed herein. Such compositions may include the purified essential oil and/or the permeate material, but also even the retentate. In a preferred embodiment, the disclosed process produces the purified essential oil. Typically, the essential oil of the invention is collected by removal of any solvent employed in the invention process.

In a preferred variation, the disclosed process produces a 90% reduction in at least one impurity, such as an agro-chemical or metal, relative to the feed essential oil. Preferably, the reduction is of a pesticide, biocide, fungicide or insecticide, such as akarizide, pyrethroide or strobilurine.

In another preferred variation, the quality of the purification of the essential oil depends on the quantity of residues of salts, the so-called dry residue, which is determined according to the European Pharmacopoeia. The inventive process showed that the dry residue could be reduced by at least 20%.

In yet another variant, the essential oil is processed to reduce the concentration of impurities in the essential oil, such as decreasing the concentration of heavy metals, preferably iron by at least 85%.

The invention, in a sixteenth aspect also relates to the purified essential oil obtained by the process of the preceding aspects and variants. As described herein, such purified oils or the solutions containing them will be less colourful, i.e. have a lower chromaticity according to CIELAB measurements.

Preferably, the lightness value L* of the purified essential oil is greater than or equal to 90, preferably greater than or equal to 95 and/or the chromaticity C* is less than or equal to 15, preferably less than or equal to 5.

In another seventeenth aspect, the invention relates to the use of a TCF nanofiltration membrane filtered essential oil for the preparation of a fine fragrance composition, a fragrance formula or a shower gel, preferably a shower gel. Preferably, these applications are colourless and/or transparent.

In another eighteenth aspect, the invention relates to a device for performing the nanofiltration process for the purification of essential oils according to any of the proceedings claims, which comprises a selectively permeable thin film composite (TFC) nanofiltration membrane with a support layer and a top layer, and wherein the TFC nanofiltration membrane does not include a nitrogen-containing polymer; and wherein the top layer is a polydimethylsiloxane; and wherein the flow rate through the first membrane is at least 8 kg [permeate]/h*m² [membrane]; and wherein the TFC nanofiltration membrane has a molecular weight cut off between 350 g/mol and 500 g/mol.

In a preferred variant, the invention relates to a device (see FIG. 14 or FIG. 15) for performing the nanofiltration process for the purification of essential oils as described above, which further comprises a flat sheet or spiral wound TFC nanofiltration membrane, a recirculation pump, a vessel for the retentate, another vessel for the permeate and a feed tank, which has a heating or cooling system depending on the used temperature. The cooling system can involve a cooling jacket or the like, preferably on the feed tank, to prevent heat transfer from the device or from the filtration process to the flowable input.

In another preferred variant, the invention relates to a device for performing the nanofiltration process for the purification of essential oils as described above, which further comprise a heat exchange unit to transfer heat, which is accrued during the filtration process at the TFC nanofiltration membrane away from the membrane area to the feed tank. This ensures that the flowable input is kept cool at a constant temperature, thus equilibrating temperatures around the cycle and ensuring mild temperature treatment, while avoiding overheating at any point during the filtration cycle.

METHODS

Figure 1:
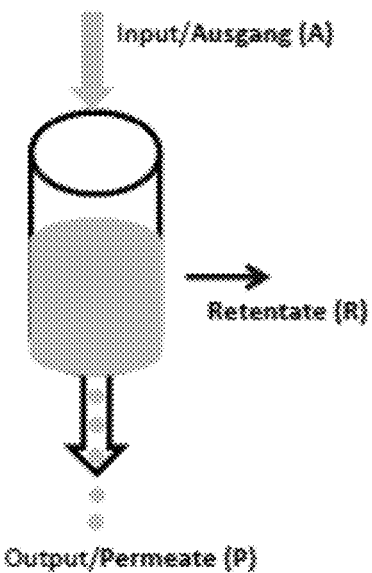
FIG. 1 is a schematic diagram of the cross-flow nanofiltration system, which explains the terms Input (A), Permeate (P) and Retentate (R) as used in the examples.

I. Colour Determination of Transparent Liquids (L*a*b*) with Spectral Photometer.

This method serves to determine the colour for transparent liquids using a spectral photometer (Lico 400 compact) from Hach Lange.

Type: Scanning grating spectrophotometer with reference beam path

Viewing geometry 0°/180° (transmitted light)

Spectral range Colour measurement: 380 nm-780 nm/10 nm,

X (red), Y (green) and Z (blue)-transmission calculated for standard illuminant C and 2° standard observer (DIN 5033)—Colour measurement (also ASTM E 170, ISO 7724)

In the L* a* b* colour system, L* is the lightness factor, a* and b* are the chromaticity coordinates (shade, saturation). a* is the position on the red-green axis and b* the position on the yellow-blue axis.

Precision validation: To ensure precision or repeatability the absolute and relative standard deviation of 6 independent measurements were calculated for the example of the 100140 lemon oil ital., lot 82 (Lico 500; QC0155). This analytical method is valid for the SAP methods AFW060 and AFW061.

II. Pesticide Screening:

The results of the above mentioned analyses are in accordance with the requirements of regulation (EC) 396/2005 (regulation on maximum residue levels of pesticides in or on food and feed) in its currently valid version.

The analysed sample can be classified as processed food which is concentrated during processing according to Article 20 of regulation (EC) 396/2005 (regulation on maximum residue levels of pesticides in or on food and feed). Therefore, the corresponding Maximum Residue Levels have to be calculated considering a concentration factor of 200.

The samples were analysed for pesticide composition by LC-MS-MS liquid chromatography method, GC-MS gas chromatography method, GC-FPD gas chromatography method with flame photometric detector or gas chromatography method with electron capture detector. The results for removal of select pesticides during filtration are shown in Table 2 and Table 5.

III. Photometric Determination of Iron:

The iron content was determined by Inductively Coupled Plasma Optical Emission Spectroscopy (ICP-OES). The Inductively Coupled Plasma (ICP) is an analytical technique to determine quantitative bulk elemental composition. The analyte species is detected and quantitated with an optical emission spectrometer (OES), which measures the intensity of radiation emitted at the element-specific, characteristic wavelength from thermally excited analyte atoms or ions. It was executed according to the DIN EN ISO 11885. The apparatus used is a Whatman, Typ Spartan 30.

The principle to determine the iron content is the reaction of Iron (III) ions with thiocyanate (rhodanide) which build a dark red colour transfer metal complex, which remains in the solution: $FeCl_3 + 6KSCN \rightarrow K_3Fe(SCN)_6 + 3\,KCl$ Procedure: The sample (1.00 ml) is put in a 10 ml measuring flask: 8.00 ml ethanol 96 vol % 1.00 ml water dist. with 0.05 ml HNO3 conc. and 1.00 ml reagent solution (KSCN 0.5 M). Shake well and measure the absorption at 465 nm after phase separation. Reference is the blank value. For the blank value mix 9.00 ml ethanol 96 vol % 1.00 ml water dist. with 0.05 ml HNO3 conc. and 1.00 ml reagent solution (KSCN 0.5 M). If there is a problem with the phase separation, filter the solution gently through a disposable membrane filter (Whatman, Typ Spartan 30, 0.45 µm).

To ensure precision or repeatability from the extinctions of the standard solutions and the corresponding iron contents (5 ppm-100 ppm) a calibration curve is prepared. This can be done with a photometric software, graphically or with Excel. The content of the samples is determined by reading the values off the calibration curve over the extinction value or calculated by the photometric software. This analytical method is valid for the SAP method AUV235.

IV. Dry Residue:

The dry residue is determined according to the European pharmacopoeia by the evaporation of the solvents of a weighing scale. A defined measure or volume (2.0 g) or (2.0 ml) of the extract are placed in the weighing scale and 3 h in a drying cabinet at 100 to 105° C. Then the residue is cooled down via phosphorus pentoxide or silica. The test result is defined in percent (m/m) or gram/liter.

VI. Peroxide Values:

The peroxide values were detected before and after the nanofiltration. The detection of peroxide gives initial evidence of rancidity in unsaturated fats and oils. It provides a measure of the extent to which an oil sample has undergone primary oxidation. The peroxide value is defined as the amount of peroxide oxygen per 1 kilogram of fat or oil. The SI units are defined in millimoles per kilogram (N.B. 1 milliequivalents=0.5 millimole; because 1 mEq of $O_2$=1 mmol/2=0.5 mmol of $O_2$, where 2 is valence).

EXAMPLES AND RESULTS

Example 1: Mandarine Oil Italian

Single-fold Mandarine oil (250 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 226 g of the oil was permeated.

The permeate flux was 91.07 kg/h*m².

Figure 2:
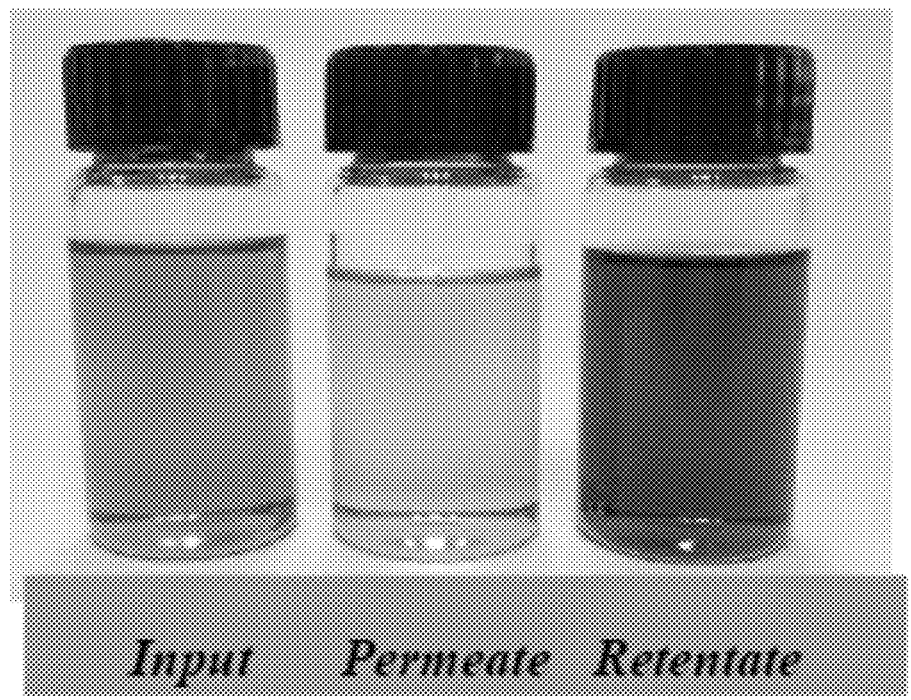
FIG. 2 (in color) shows the differences between Input (A), Permeate (P) and Retentate (R) Samples of Mandarine oil before and after nanofiltration according to Example 1.

FIG. 2 shows the differences between Input (A), Permeate (P), and Retentate (R) samples of Mandarine oil before and after nanofiltration

TABLE 1

CIELAB-Results of Mandarine Oil before and after nanofiltration

| CIELAB-Results: | L* | A* | B* |
|---|---|---|---|
| Flowable input | 90.9 | −3.0 | 133.9 |
| Permeate | 93.1 | −10.0 | 128.5 |

Table 1 and FIG. 2 show that the colour of the permeate samples was decreased in contrast to the flowable input and the retentate. These results demonstrate the advantages of the inventive process to reduce the colour of essential oils, including citrus oils, especially Mandarine oil.

According to Tab. 1 the difference of ΔL* between permeate after nanofiltration to the flowable input is 2.2 and ΔC* could be calculated as −5.0.

The results from the fragrance test showed that the odour of the Mandarine oil is stronger, with sparking and transparent note, especially the aldehyde part is stronger.

Figure 3:
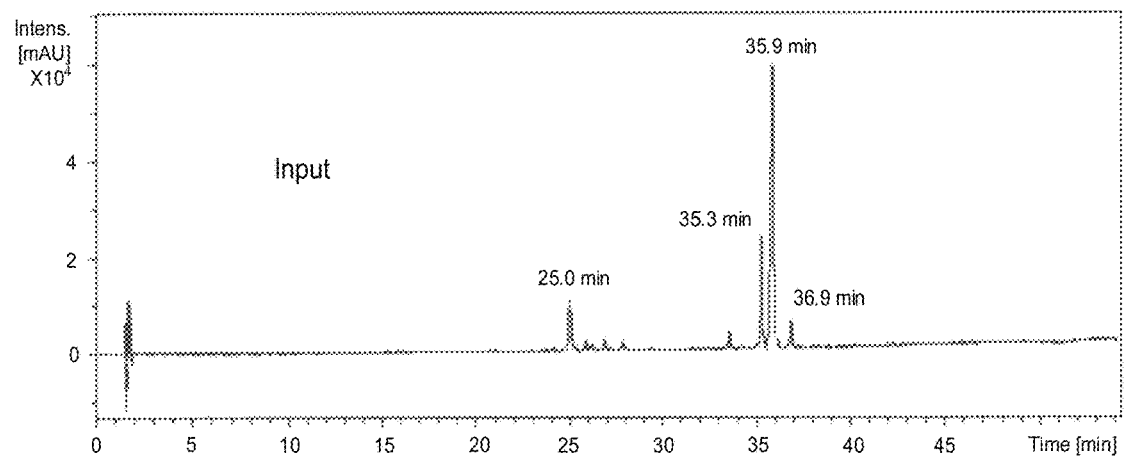
FIG. 3 shows the HPLC/MS-analysis of Input (A), Permeate (P) and Retentate (R) Samples of Mandarine oil.
Figure 3:
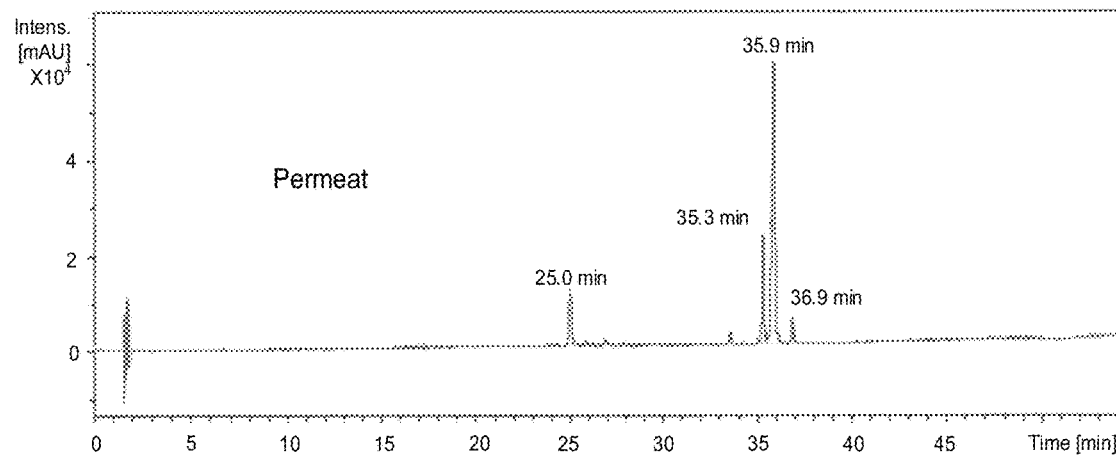
Figure 3:
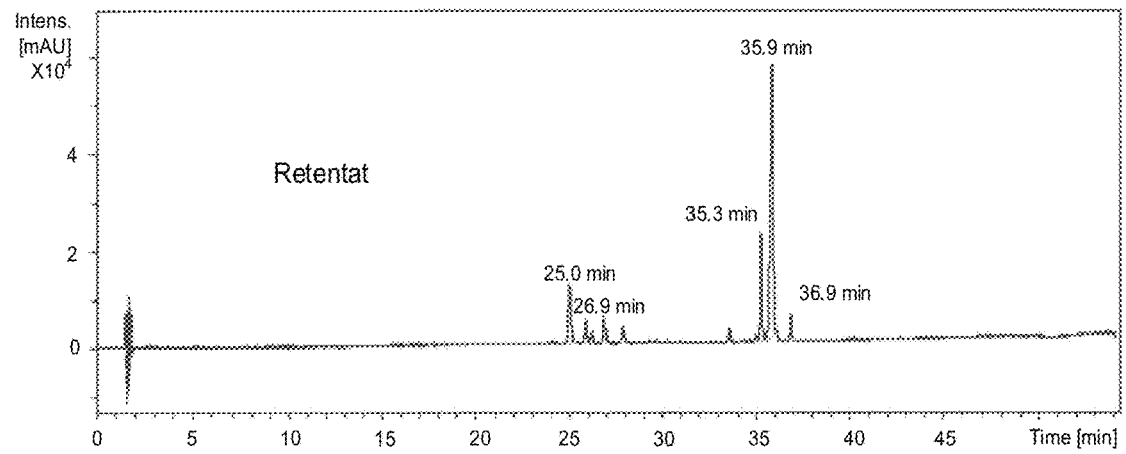

The results from HPLC/MS-analysis of input, permeate and retentate samples of Mandarine oil are shown in FIG. 3. The intensity of impurities in the retentate are higher than in permeate, while they are reduced in the permeate as compared to the input.

Samples of the feed (flowable input), retentate and permeate solutions were taken to determine the concentration of pesticides (agrochemical residues) present in the solutions. The pesticide screening of Mandarine oil Italian shows the removal of selected pesticides and fungicides through the TFC nanofiltration in Table 2.

TABLE 2

Concentration of select pesticides in Input, Retentate and Permeate solutions of Mandarine Oil and maximum residue level of the pesticides

| Compound | Input | Retentate | Permeate | Maximum Residue Level mg/kg |
|---|---|---|---|---|
| Organochlorine Pesticides and Pyrethroides | | | | |
| p,p-Dicofol | 0.093 | 0.12 | — | 4 |
| Organophosphorus Pesticides (Citrus Oils) | | | | |
| Chlorpyrifos | Traces <0.1 | Traces <0.1 | — | 60 |
| Organonitrogen Pesticides Pesticide Screening LC-MS/MS | | | | |
| Pyraclostrobin | Traces <0.1 | 0.11 | — | 200 |

The data shows that with the present invention, fungicides, including strobilurine, especially pyraclostrobin are almost completely removed from the essential oil with the inventive process and the TFC nanofiltration membrane. Further reductions in agrochemical residues (pesticides), including organochlorine, especially p,p-Dicofol (acaricide) and organophosphorus, especially chlorpyrifos could be achieved.

Also naturally occurring impurities could be removed, preferably furocoumarine, such as oxypeucedanin, heraclenin, byak-angelicol, 8-Geranyloxypsoralen or Imperatorin were removed.

Example 2: Vanilla Extract—Fair Trade 10-fold Vanilla extract (200 g) diluted with ethanol/water 95/5 was filtered at a temperature of 40° C. and filtration pressure of 30 bar with a spiral or flat sheet PDMS-GMT-NC-1 membrane with a nominal molecular weight cut-off of approximately 350 g/mol. The permeate flux was 8.57 kg/h*m². As a result, 312 g of the diluted oil was permeated. The solvent was removed under vacuum.

Figure 4:
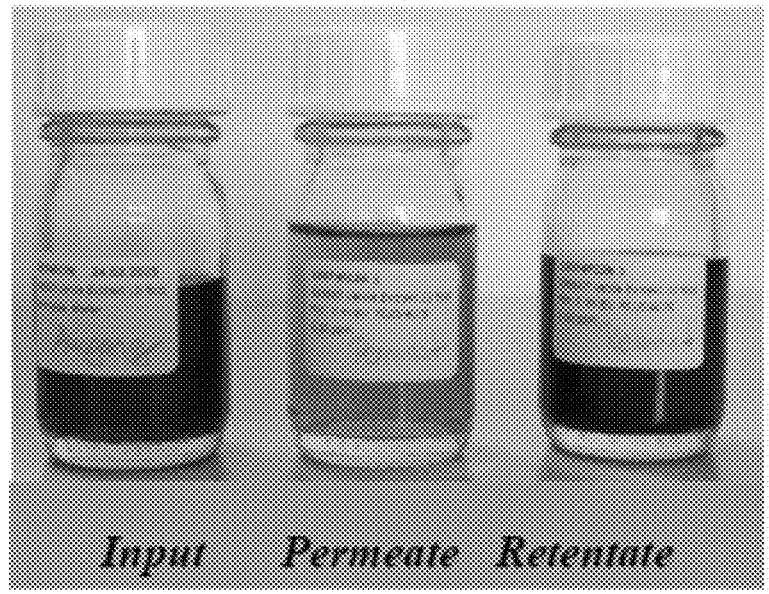
FIG. 4 (in color) shows the differences between Input (A), Permeate (P) and Retentate (R) of Vanilla Extract before and after nanofiltration according to Example 2.

FIG. 4 shows the differences between Input (A), Permeate (P), and Retentate (R) samples of Vanilla extract before and after nanofiltration. The colour was reduced in the permeate for the Vanilla extract sample.

The results from the fragrance test showed the vanilla character to be more recognizable.

Example 3a: Patchouli Oil without Solvent

Single-fold Patchouli oil (250 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 208 g of the oil was permeated. The permeate flux was 14.14 kg/h*m².

Figure 5:
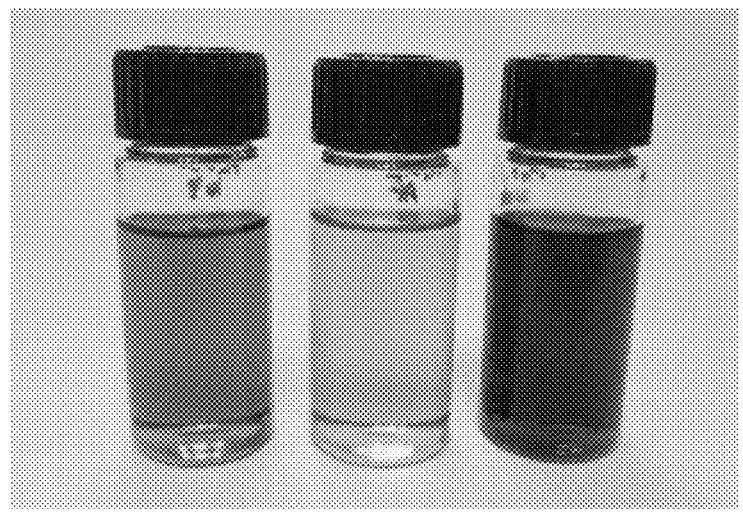
FIG. 5 (in color) shows the differences between Input (A), Permeate (P) and Retentate (R) of Patchouli oil (Example 3a) before and after nanofiltration.

FIG. 5 shows the differences between Input (A), Permeate (P), and Retentate (R) of Patchouli oil before and after nanofiltration.

Example 3b: Patchouli Oil with Solvent

Single-fold Patchouli oil (180 g) dissolved in 70 g MTBE was filtered at a temperature of 30° C. and filtration pressure of 30 bar with a spiral or flat sheet PDMS-GMT-NC-1 membrane with a nominal molecular weight cut-off of approximately 350 g/mol. As a result, 210 g of the oil was permeated. MTBE was removed under vacuum and with 50 ml ethanol casted out. The permeate flux was 53.57 kg/h*m².

Figure 6:
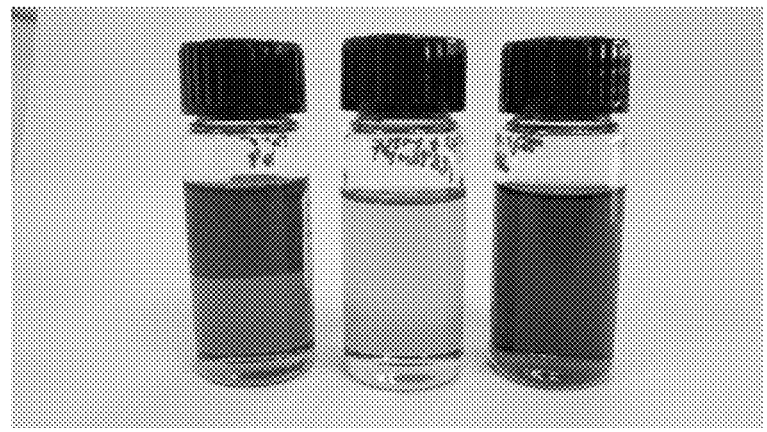
FIG. 6 (in color) shows the differences between Input (A), Permeate (P) and Retentate (R) of Patchouli oil with solvent (Example 3b) before and after nanofiltration with solvent.

FIG. 6 shows the differences between Input (A), Permeate (P), and Retentate (R) of Patchouli oil with solvent before and after nanofiltration with solvent.

TABLE 3

CIELAB-Results of Patchouli oil after nanofiltration

| CIELAB-Results: | L* | A* | B* |
|---|---|---|---|
| Flowable Input | 93.4 | −11.8 | 49.2 |
| Permeate | 96.3 | −11.8 | 35.0 |

FIG. 6 and table 3 demonstrate the reduction in colour of essential oil, especially Patchouli oil. Although the flux was three to four times faster, the selective reduction of coloured impurities was just as good as when the flux was slower without solvent. The faster flux lead to a faster production process and, therefore, energy costs can be saved.

According to Tab. 3 the difference $\Delta L^*$ of permeate (after nanofiltration) to the flowable Input is 2.9 and $\Delta C^*$ could be calculated as −13.7.

The results from the fragrance test showed the patchouli oil character is more recognizable and that the patchouli part has more volume and is stronger. The results from the fragrance test of the purified Patchouli oil without solvent was not as good as the result of the purified Patchouli oil with solvent.

TABLE 4

Iron content in Patchouli oil before and after nanofiltration

| Iron-Content in (ppm): | Input | Permeate | Retentate |
|---|---|---|---|
| 1. Measurement | 267 | 40 | 916 |
| 2. Measurement | 259 | 23 | 729 |

The results show that the iron content in permeate was reduced about 230 ppm (more than 84%) through the nanofiltration with a solvent.

Example 4: Orange Oil Brasil

Ten-fold Orange oil (202 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 68 g of the oil was permeated. The permeate flux was slow 19.29 kg/h*m².

Figure 7:
FIG. 7 (in color) shows the differences between Input (A), Permeate (P) and Retentate (R) of Orange oil Brasil (Example 4) before and after nanofiltration.

FIG. 7 shows the differences between Input (A), Permeate (P), and Retentate (R) of Orange oil Basil before and after nanofiltration.

These results demonstrate the potential to reduce the colour of essential oils, including citrus oils, especially orange oil.

The results from the fragrance test showed that the zesty part of orange was kept and that the Bench Mark is different and less good.

Pesticide Screening: Orange Oil Brasil

TABLE 5

Concentration of select pesticides in Input, Retentate and Permeate solutions from Orange oil Brasil and maximum residue level of the pesticides

| Compound | Input | Retentate | Permeate | Maximum Residue Level mg/kg |
|---|---|---|---|---|
| Organochlorine Pesticides and Pyrethroides | | | | |
| Bifenthrin | 0.71 | 1.4 | 0.43 | 20 |
| Cyfluthrin | — | 0.29 | — | 4 |
| Cypermethrin | — | 0.26 | — | 400 |
| Organophosphorus Pesticides (Citrus Oils) | | | | |
| Chlorpyrifos | 2.6 | 3.9 | 2.1 | 60 |
| Methidathion | — | 0.12 | — | 4 |
| Organonitrogen Pesticides (ON/HT) | | | | |
| Propargite | 1.8 | 4.1 | 1.0 | 2 |
| Pesticide Screening LC-MS/MS | | | | |
| Azoxystrobin | 0.17 | 0.3 | — | 3000 |
| Diflubenzuron | 0.19 | 0.47 | 0.11 | 200 |
| Phosmet | 0.14 | — | 0.11 | 100 |
| Pyraclostrobin | 0.35 | 0.74 | 0.22 | 400 |
| Trifloxystrobin | 0.68 | 1.4 | 0.43 | 100 |

The data show that with the present invention fungicides, including strobilurine, especially azoxystrobin, pyraclostrobin and trifloxystrobin are almost completely removed from the oil with the inventive process. Further reductions in agrochemical residue (pesticides), including organophosphorus pesticides, especially chlorpyrifos and methidathion, and organonitrogen pesticides, especially propargite, could be achieved. Furthermore, insecticides (pyrethroides), especially bifenthrin, cyfluthrin and cypermethrin, are reduced. This example demonstrates the removal of agrochemical residues from essential oils.

Example 5: Benzoin Siam Resin

Benzoin siam oil (50 g) diluted in 200 g ethanol was filtered at a temperature of 30° C. and filtration pressure of 30 bar with a spiral or flat sheet PDMS-GMT-NC-1 membrane with a nominal molecular weight cut-off of approximately 350 g/mol. As a result, 58 g of the oil was permeated. The permeate flux was 21.43 kg/h*m$^2$.

These results demonstrate the reduction in colour of the essential oil.

The results from the fragrance test showed that the Benzoin siam character was stronger and more floral.

Example 6: Peru Balsam

Peru balsam oil (200 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 90 g of the oil was permeated. The permeate flux was 8.57 kg/h*m$^2$.

Figure 8:
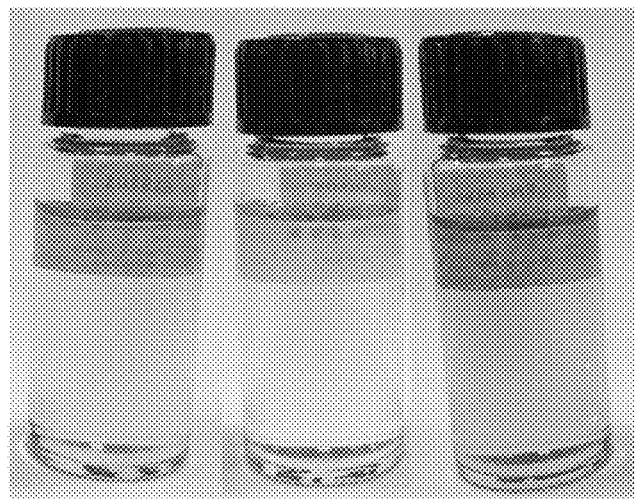
FIG. 8 (in color) shows the differences between Input (A), Permeate (P) and Retentate (R) of Peru Balsam (Example 6) before and after nanofiltration.

FIG. 8 shows the differences between Input (A), Permeate (P) and Retentate (R) of Peru Balsam (Example 6) before and after nanofiltration These results demonstrate the reduction in colour of the essential oil.

The results from the fragrance test showed that the character was more cinnamic, spicy and more sweet.

Example 7: Crude Blood Orange Oil Italian

Blood orange oil (20 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 16 g of the oil was permeated.

The permeate flux was 64.29 kg/h*m$^2$.

Naturally occurring impurities could be removed, in particular furocoumarines, such as oxypeucedanin, heraclenin, byak-angelicol, 8-geranyloxypsoralen or imperatorin were removed.

Figure 9:
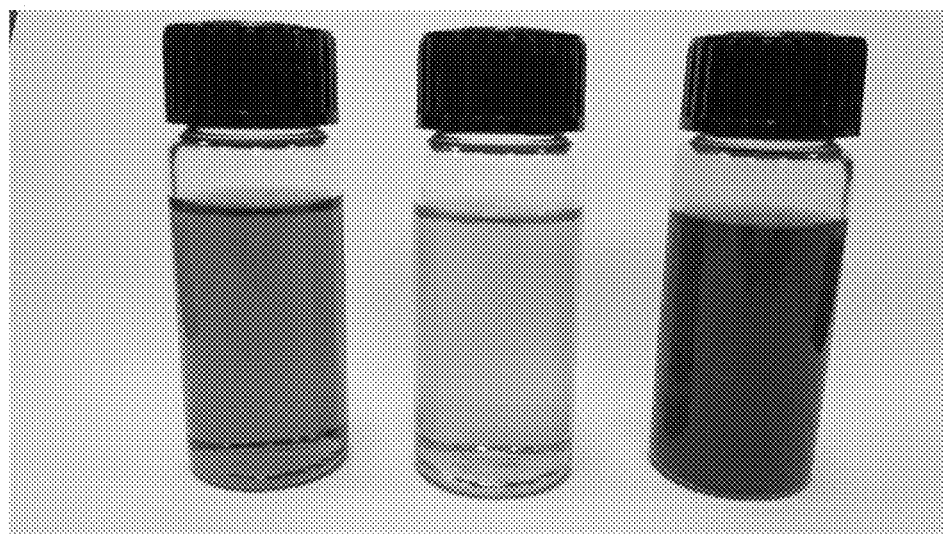
FIG. 9 (in color) shows the differences between Input (A), Permeate (P) and Retentate (R) of Blood Orange oil Italian (Example 7) before and after nanofiltration.

FIG. 9 shows the differences between Input (A), Permeate (P) and Retentate (R) of blood orange oil before and after nanofiltration These results demonstrate the reduction in colour of the essential oil.

The results from the fragrance test showed that the blood orange character was weaker than before nanofiltration. The retentate showed stronger blood orange character than permeate and flowable input.

Example 8: Tangerine Oil

Tangerine oil (263 g) was filtered at a temperature of 30° C. and filtration pressure of 30 bar with a spiral or flat sheet PDMS-GMT-NC-1 membrane with a nominal molecular weight cut-off of approximately 350 g/mol. As a result, 51 g of the oil was permeated. The permeate flux was 64.29 kg/h*m$^2$.

Figure 10:
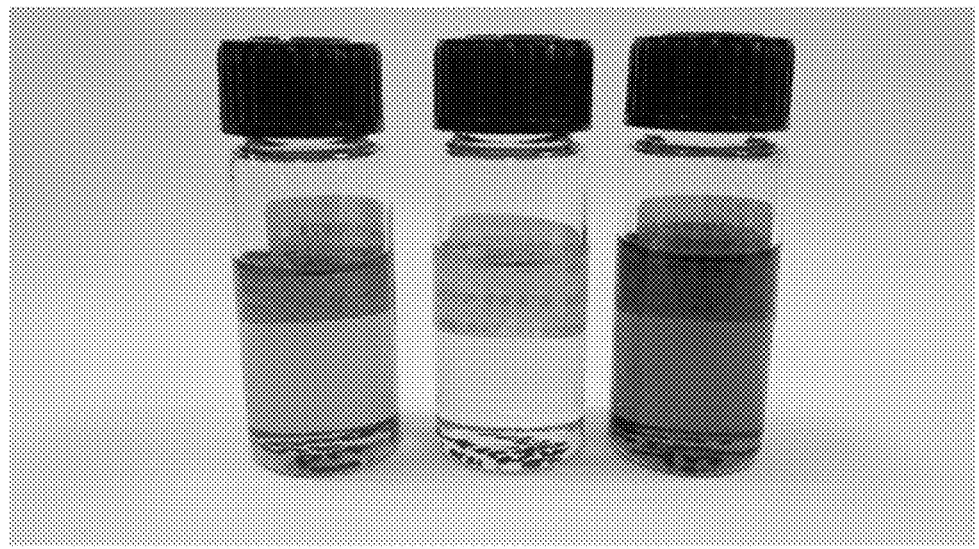
FIG. 10 (in color) shows the differences between Input (A), Permeate (P) and Retentate (R) of Tangerine oil Italian (Example 8) before and after nanofiltration.

FIG. 10 shows the differences between Input (A), Permeate (P) and Retentate (R) of Tangerine oil before and after nanofiltration.

These results demonstrate the reduction in colour of the essential oils, including citrus oils, especially tangerine oil.

TABLE 6

CIELAB-Results of Tangarine Oil before and after nanofiltration

| CIELAB-Results: | L* | A* | B* |
|---|---|---|---|
| Flowable Input | 94.7 | −10.9 | 102.2 |
| Permeate | 100.7 | −5.1 | 11.0 |

According to Tab. 6 the difference of ΔL* of the permeate after nanofiltration to the flowable input is 6.0 and ΔC* could be calculated as −90.7. There was a considerable reduction in colour.

TABLE 7

CIELAB-Results of Tangarine Oil before and after nanofiltration as well as the permeate after 48 h exposure to UV-light

| CIELAB-Results: | L* | A* | B* |
|---|---|---|---|
| Flowable Input | 98.7 | −8.1 | 27.5 |
| Permeate | 100.0 | −0.4 | 1.3 |
| Permeate after 48 h exposer to UV- light | 99.9 | −0.4 | 0.8 |

According to Tab. 7 the difference of ΔL* of the permeate after nanofiltration to the flowable input is 1.3 and ΔC* could be calculated as −27.3.

The difference of ΔL* of permeate after nanofiltration to the permeate after nanofiltration+UV-light is −0.1 and ΔC* could be calculated as 0.47. Evidently, the lightness only dropped slightly as compared to the freshly filtered permeate. In addition, the chromaticity was stable after 48 h UV-light and did not re-colour.

The results from the fragrance test showed that the character was less terpenic, more natural and dimethylanthranilate is less present. The GC/MS-analysis showed that the amount of decanal was reduced.

The results from the peroxide value test showed that the tangerine peroxide value dropped from 7.72 mEq of $O_2$/kg (before TFC nanofiltration) to 5.37 mEq of $O_2$/kg after TFC nanofiltration. These results demonstrate the potential to reduce the rancidity of essential oils, including citrus oils, especially tangerine oil.

The dry residue is determined according to the European pharmacopoeia by the evaporation of the solvents of a weighing scale. A defined measure or volume (2.0 g) or (2.0 ml) of the extract are placed in the weighing scale and 3 h in a drying cabinet at 100 to 105° C. Then the residue is cooled down via phosphorus pentoxide or silica. The test result is defined in percent (m/m) or gram/liter.

The dry residue from Tangerine oil 2.2% (before TFC nanofiltration) to 0.47% after TFC nanofiltration showed that impurities were reduced by the inventive process.

Example 9: Lemon Oil Italian

Lemon oil was purified according to the method described for example 1 without solvent. The permeate flux was 71.14 kg/h*m².

Figure 11:
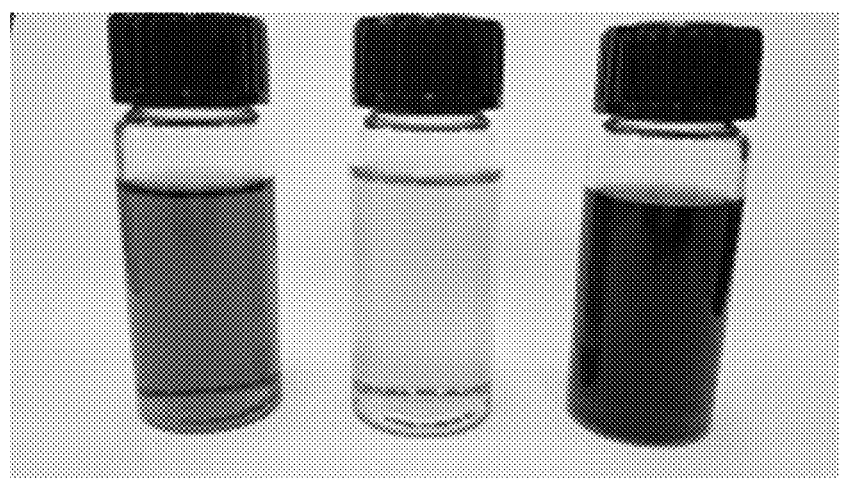
FIG. 11 (in color) shows the differences between Input (A), Permeate (P) and Retentate (R) of Lemon Oil Italian (Example 9) before and after nanofiltration.

FIG. 11 shows the differences between Input (A), Permeate (P) and Retentate (R) of Lemon oil before and after nanofiltration.

These results demonstrate the reduction in colour of the essential oils, including citrus oils, especially lemon oil.

Also naturally occurring impurities could be removed, preferably furocoumarine, such as oxypeucedanin, 8-geranyloxypsoralen or bergamottin were removed.

The results from the fragrance test showed that the character was cold smoke, cigarette, and coffee.

Example 10: Clove Leaves Oil

Clove leaves oil was purified according to the method described for example 1 without solvent. The permeate flux was 12.64 kg/h*m².

Figure 12:
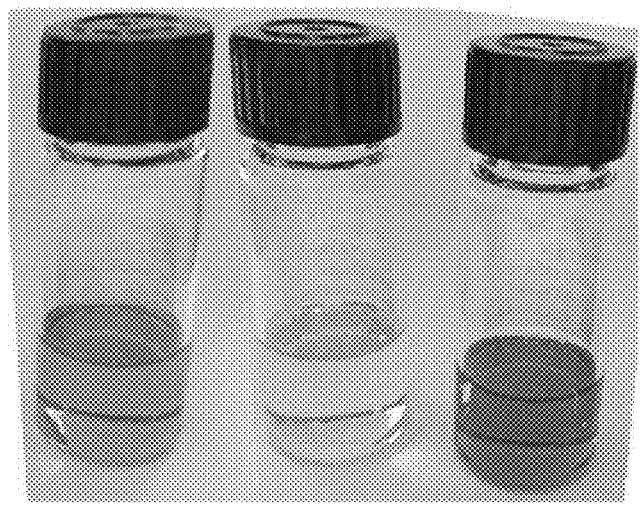
FIG. 12 (in color) shows the differences between Input (A), Permeate (P) and Retentate (R) of Clove leaves (Example 10) before and after nanofiltration.

FIG. 12 shows the differences between Input (A), Permeate (P) and Retentate (R) of Clove leaves oil before and after nanofiltration.

These results demonstrate the reduction in colour of the clove leaves oil.

The results from the fragrance test showed that the character of clove leaves was more recognizable after nanofiltration than before.

Example 11: Ylang Ylang Oil

Ylang Ylang oil was purified according to the method described for example 1 without solvent. The permeate flux was 24.00 kg/h*m2.

Figure 13:
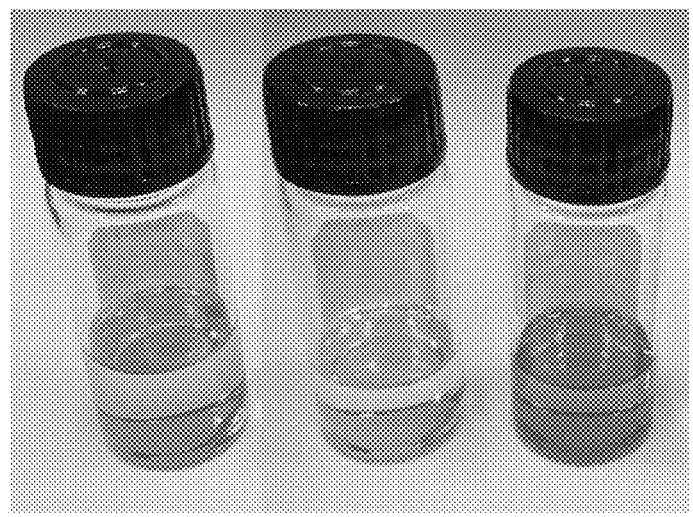
FIG. 13 (in color) shows the differences between Input (A), Permeate (P) and Retentate (R) of Ylang Ylang (Example 11) before and after nanofiltration.
Figure 14:
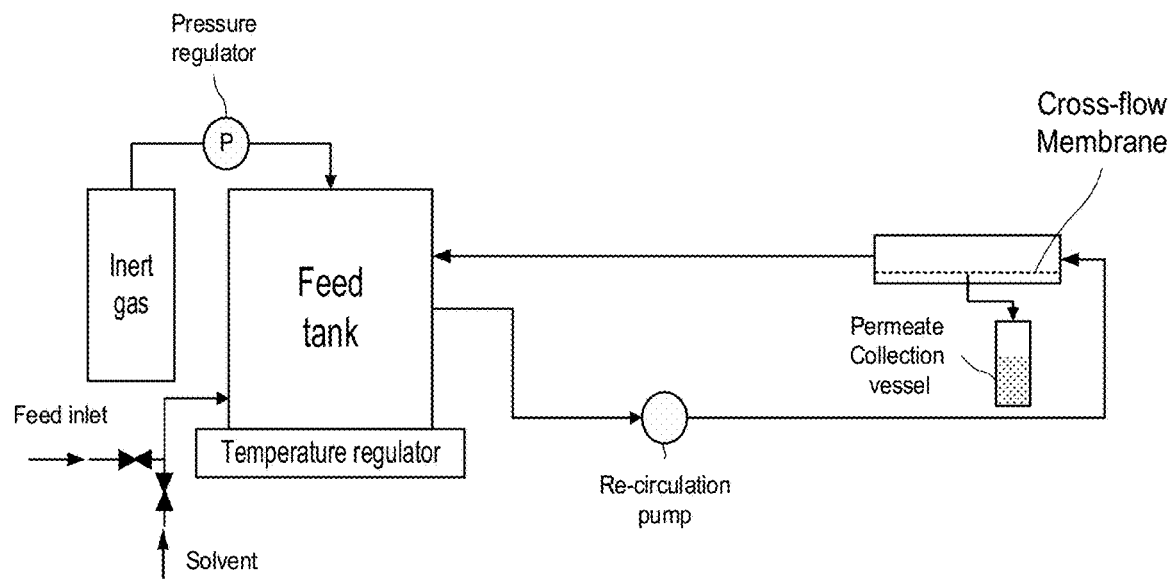
FIG. 14 is a schematic diagram (Flow chart) of the cross-flow nanofiltration system describing the purification process of the essential oils, to produce Permeate (P) and Retentate (R), working with external pressure ($N_2$), containing one flat sheet crossflow filtration cell.
Figure 15:
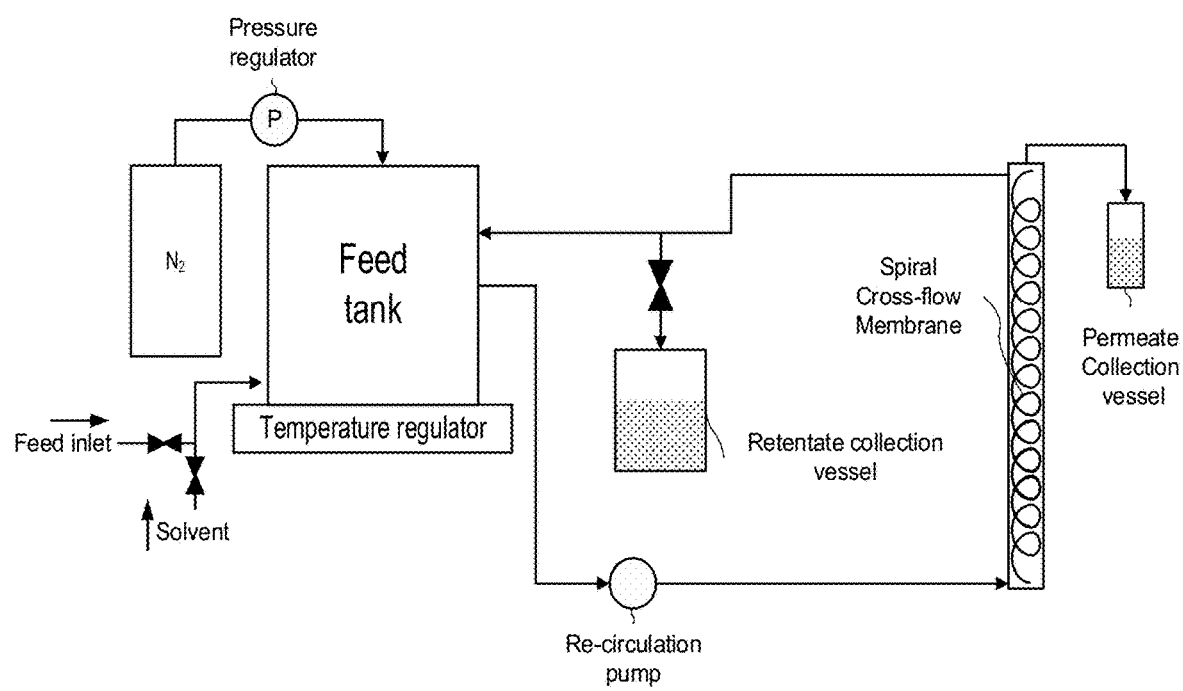
FIG. 15 is a schematic diagram (Flow chart) of the cross-flow nanofiltration system describing the purification process of essential oils, producing Permeate (P) and Retentate (R), working with or without external pressure (N₂) (in-build pump develops pressure), containing one spiral filtration cell.

FIG. 13 shows the differences between Input (A), Permeate (P) and Retentate (R) of Ylang Ylang oil before and after nanofiltration.

These results demonstrate the reduction in colour of the Ylang Ylang oil.

The results from the fragrance test showed that the character was more floral and exotic, more salicylate. The difference before and after nanofiltration is obvious.

TABLE 8

Overview of the calculated CIELAB values ΔL* and ΔC*:

| Example | Compound | L* | ΔL* | C* | ΔC* |
|---|---|---|---|---|---|
| 1 | Mandarine Oil (flowable input) | 90.9 | 2.2 | 133.9 | −5.0 |
| 1 | Mandarine Oil (permeate) | 93.1 | | 128.9 | |
| 3a | Pachtouli Oil (flowable input) | 93.4 | 2.9 | 50.6 | −13.7 |
| | Pachtouli Oil (permeate) | 96.3 | | 36.9 | |
| 8a | Tangerine Oil (flowable input) | 94.7 | 6.0 | 102.8 | −90.7 |
| 8a | Tangerine Oil (permeate) | 100.7 | | 12.1 | |
| 8b | Tangerine Oil (flowable input) | 98.7 | 1.3 | 28.7 | −27.3 |
| | Tangerine Oil (permeate) | 100.0 | | 1.4 | |
| 8b | Tangerine Oil (after filtration + 48 h UV-light) | 99.9 | −0.1 | 0.9 | 0.47 |

Table 8 shows the difference of ΔL* and ΔC* of the permeate after nanofiltration to the flowable input. In each example there was an evident increase in the lightness and decrease in the colourfulness after filtration, which demonstrates the efficacy of the purification method. For the UV-stability test of the permeate there was no significant change in the lightness and colourfulness, which means there was no re-colouration.

TABLE 9

Showing example 9, Mandarine Oil and Orange Oil purified according to the invention in a colourless Fine Fragrance.

| | comparison | filtered EO |
|---|---|---|
| MANDARINE COLD TREATMENT | | 30 |
| ORANGE BRAS COLD TREATMENT | | 125 |
| BERGAMOT ECO ESSENCE (E0636) W/O MYRCENE | 200 | 200 |
| LINALYL ACETATE | 25 | 25 |
| LEMON OIL WINTER ITALIE | 50 | 50 |
| ORANGE OIL | 125 | |
| MANDARIN OIL ITAL. | 30 | |
| GRAPEFRUIT OIL | 50 | 50 |
| PEPPER OIL BLACK PERF. | 10 | 10 |
| RED BERRY EXTR. | 5 | 5 |
| HELIONAL | 20 | 20 |
| HYDROXY CITRONELLAL | 10 | 10 |
| GERANYL ACETATE PURE | 5 | 5 |
| BENZYL ACETATE | 5 | 5 |
| HEDIONE | 100 | 100 |
| HEDIONE HC/70 | 50 | 50 |
| HEXYL CINNAMIC ALDEHYDE ALPHA | 130 | 130 |
| ISORALDEINE 95 | 15 | 15 |
| ISO E SUPER | 20 | 20 |
| VETIVEROL | 10 | 10 |
| PATCHOULI OIL DECOL. MD | 50 | 50 |
| ELEMI OIL | 10 | 10 |
| AURELIONE ® | 20 | 20 |
| ETHYLENE BRASSYLATE | 30 | 30 |
| GALAXOLIDE 50% IN IPM | 30 | 30 |
| Parts in g: | 1,000.000 | 1,000.000 |

The test preparation of a colourless fine fragrance demonstrated that the final composition including the filtered essential oil was visually colourless and transparent to the observer.

TABLE 10

Showing example 10, Mandarine Oil and Orange Oil purified according to the invention in a colourless Showergel.

|  | comparison | filtered EO |
|---|---|---|
| MANDARINE COLD TREATMENT |  | 25 |
| ORANGE BRAS COLD TREATMENT |  | 300 |
| ALDEHYDE C 8 | 0.5 | 0.5 |
| HEXENYL ACETATE CIS-3 | 4 | 4 |
| ORANGE OIL | 300 |  |
| MANDARIN OIL ITAL. | 25 |  |
| GRAPEFRUIT OIL | 20 | 20 |
| PEPPER OIL BLACK PERF. | 5 | 5 |
| FIR NEEDLE SIBERIA H | 10 | 10 |
| ISOAMYL ACETATE | 0.5 | 0.5 |
| DECALACTONE GAMMA | 5.5 | 5.5 |
| ETHYL METHYL BUTYRATE-2 | 1 | 1 |
| ETHYL MALTOL | 1 | 1 |
| DAMASCONE ALPHA | 3 | 3 |
| DAMASCONE DELTA | 0.5 | 0.5 |
| IONONE BETA | 35 | 35 |
| CLOVE LEAF OIL DECOL. | 5 | 5 |
| AGRUMEX LC | 70 | 70 |
| KOAVONE | 80 | 80 |
| ORYCLON SPECIAL | 120 | 120 |
| CEDARWOOD OIL | 60 | 60 |
| CEDARWOOD OIL CHIN. | 15 | 15 |
| PATCHOULI OIL DECOL. MD | 85 | 85 |
| ISOLONGIFOLANON COEUR | 85 | 85 |
| AMBROCENIDE ® CRYST. 10% IPM | 1.5 | 1.5 |
| MACROLIDE ® SUPRA | 5 | 5 |
| DIPROPYLENE GLYCOL | 62.5 | 62.5 |
| Parts in g: | 1,000.000 | 1,000.000 |

The test preparation of a colourless shower gel demonstrated that the final composition including the filtered essential oil was visually colourless and transparent to the observer.

TABLE 11

Data overview of the results of all purified essential oils:

| Expl. | Compound | CIE LAB | ΔL* | ΔC* | Photo | Impurities | Flow rate | Extra Test | Fragrance |
|---|---|---|---|---|---|---|---|---|---|
| 1 | Mandarine oil Italian (Single-fold) | L, A, B | 2.2 | −5.0 | FIG. 3 | Pesticide Furocoumarine | 91.07 kg/h*m$^2$ | HPLC/MS-analysis Fine Fragrance + Shower-gel | odour of mandarin oil stronger, with sparking transparent note, aldehyde part is stronger |
| 2 | Vanilla extract (10-f) |  |  |  | FIG. 4 |  | 8.57 kg/h*m$^2$ |  | vanilla character more recognizable |
| 3a | Patchouli oil + MTBE | L, A, B | 2.9 | −13.7 | FIG. 5 | Iron | 14.14 kg/h*m$^2$ |  | 3b is better than 3a |
| 3b | Patchouli oil (−) Solvent |  |  |  | FIG. 6 |  | 53.57 kg/h*m$^2$ |  | More patchouli character, more volume, stronger. |
| 4 | Orange oil Brasil (10-fold) |  |  |  | FIG. 7 | Pesticides | 19.29 kg/h*m$^2$ | Fine Fragrance + Shower-gel | Maintained zesty part of orange; Bench Mark is different and less good |
| 5 | Benzoe Siam oil + MTBE |  |  |  |  |  | 21.43 kg/h*m$^2$ |  | More floral and more stronger |
| 6 | Peru Balsam |  |  |  | FIG. 8 |  | 8.57 kg/h*m$^2$ |  | More cinnamic, spicy and more sweet. |
| 7 | Blood Orange Oil |  |  |  | FIG. 9 | Furocoumarine | 64.29 kg/h*m$^2$ |  | Weaker than before nanofiltration. Retentate is more stronger than Permeate and Input |
| 8a 8b | Tangerine Oil | L, A, B | 6.0 | −90.7 | FIG. 10 |  | 64.29 kg/h*m$^2$ | Peroxide Dry Residue | Less terpenic, and more natural, dimethylanthranilate is less present. |
|  |  | L, A, B +48 h UV-light | 1.3 −0.1 | −27.3 0.47 |  |  |  |  |  |
| 9 | Italian Lemon Oil |  |  |  | FIG. 11 | Furocoumarine | 71.14 kg/h*m$^2$ |  | Cold smoke, cigarette, coffee, very interesting. |
| 10 | Clove leaves Oil |  |  |  | FIG. 12 |  | 12.64 kg/h*m$^2$ |  | After nanofiltration is better than not filtrated |
| 11 | Ylang Ylang oil |  |  |  | FIG. 13 |  | 24.00 kg/h*m$^2$ |  | More floral and exotic, more salicylate. The difference is obvious |

The data in the tables and figures demonstrate the reduction in colour of the essential oils filtered, preferably citrus oils. Especially the difference of ΔL* and of ΔC* of permeate after nanofiltration as compared to the flowable input shows that the essential oils had less chromaticity. Further, the results from the HPLC/MS-analysis of input, permeate and retentate samples of Mandarine oil showed that the intensity of the impurities could be reduced in the permeate while they were higher in the retentate. The pesticide screening of the essential oils showed the removal of selected pesticides and fungicides through the TFC nanofiltration. Also the iron content could be reduced and the peroxide value dropped. The dry residue of the permeate was less than of the flowable input and high molecular weight components and waxes could be removed. These results show that the inventive process delivers purified essential oils which can be used as fine fragrances, fragrance ingredients or flavours, especially in colourless or transparent compositions. Also the results from fragrance tests showed that the odour of the essential oils was more prominent while bad odours could be removed and suppressed.

The invention claimed is:

1. A nanofiltration process for purifying an essential oil for a fragrance, flavour or cosmetic ingredient by removing synthetic pesticide or fungicide impurities, comprising the following steps:
   (i) providing a selectively permeable thin film composite (TFC) nanofiltration membrane, wherein the membrane consists of a top layer and a more porous chemically different layer, wherein the top layer comprises a material selected from the group consisting of polyoctylmethylsiloxane, poly[1-(trimethylsilyl)-1-propyne], poly(2,6-dimethyl-1,4-phenylene oxide), polyacrylonitrile, polymer of intrinsic microporosity (PIM-1), polystyrene-b-poly(ethylene oxide) diblockcopolymer, poly(sodiumstyrenesulphonate) (PSS) or polyvinylsulphate (PVS) and mixtures thereof
   and wherein the TFC nanofiltration membrane has a molecular weight cut-off of between 150 g/mol and 1200 g/mol;
   (ii) providing a flowable input of essential oil, with a solvent component;
   (iii) separating the flowable input by transferring it across the surface of the membrane to form a retentate and a permeate, such that the concentration of one or more components of the permeate is reduced compared to the flowable input; wherein the flow rate through the membrane is at least 8 kg [permeate]/h*m2 [membrane];
   and wherein the permeate is decoloured in comparison to the flowable input, such that the lightness value L* of the permeate is increased in comparison to the flowable input to ΔL* greater than or equal to 1 and the chromaticity C* of the permeate is decreased in comparison to the flowable input to ΔC* less than or equal to −2, according to the CIELAB colour measurement system, as specified by the International Commission on Illumination;
   (iv) collecting the permeate and removing the solvent.

2. The process according to claim 1, wherein the lightness value L* of the permeate is increased in comparison to the flowable input to ΔL* greater than or equal to 1.5, and/or the chromaticity C* of the permeate is decreased in comparison to the flowable input to ΔC* less than or equal to −4.

3. The process according to claim 1, wherein the colour stability of the permeate is such that the re-colouration measured by the change in lightness of the permeate 48 h after nanofiltration in comparison to the permeate just after nanofiltration is only decreased to ΔL* greater than or equal to −1.0, and/or the chromaticity C* of the permeate 48 h after nanofiltration is only increased in comparison to the permeate after nanofiltration to ΔC* less than or equal to 10.

4. The process according to claim 1, wherein the more porous chemically different layer of the TFC nanofiltration membrane comprises a polymer which includes one or more of the heteroatoms O, N, S, and/or halogen, and/or Si.

5. The process according to claim 1, wherein the more porous chemically different layer comprises a material chosen from the group consisting of: polydimethylsiloxane, polyoctylmethylsiloxane, poly[1-(trimethylsilyl)-1-propyne], polytetrafluoroethylene, polysulfone, polyethersulfone, polyvinylidene fluoride and polyetheretherketone.

6. The process according to claim 1, wherein the solvent component comprises an organic solvent, and the organic solvent has a dipole moment of at least $4*10^{-30}$ Cm.

7. The process according to claim 6, wherein the organic solvent used to prepare the flowable input is chosen from the group consisting of: diethyl ether, ethanol, isopropanol, ethyl acetate, methylethylketone, butylacetat, methyl-tert-butyl-ether, cyclohexanol and acetone.

8. The process according to claim 7, wherein the organic solvent used to prepare the flowable input is chosen from methyl-tert-butyl-ether and ethanol.

9. The process according to claim 1, wherein the solvent further comprises a second organic solvent component, which has a dipole moment of less than $2*10^{-30}$ Cm.

10. The process according to claim 9, wherein the essential oil is chosen from the group consisting of: mandarine oil, peru balsam, tangerine oil, blood orange oil, patchouli oil, vanilla extract and benzoin siam oil.

11. The process according to claim 1, wherein the essential oil is derived from the genus Citrus.

12. The process according to claim 1, wherein the lightness value L* of the permeate is increased in comparison to the flowable input to ΔL* greater than or equal to 2.0, and/or the chromaticity C* of the permeate is decreased in comparison to the flowable input to ΔC* less than or equal to −10.

13. The process according to claim 1, wherein the essential oil is chosen from the group consisting of: sweet orange, orange, lemon, lime, grapefruit, bergamot, key lime, pomelo, citron, mandarine, tangerine, bitter orange, blood orange and/or wherein the essential oil is selected from the group consisting of: peru balsam oil, benzoin siam oil, patchouli oil, rose oil, ylang oil, clove leaves, lemon oil, oak moss absolute and vanilla extract.

14. A system for performing the nanofiltration process for the purification of essential oils according to claim 1, comprising the selectively permeable thin film composite (TFC) nanofiltration membrane with the more porous chemically different layer and the top layer, wherein the TFC nanofiltration membrane comprises a polymer, which includes one or more heteroatom selected from O, N, S, and/or halogen and/or Si; wherein the top layer comprises a material selected from the group consisting of polyoctylmethylsiloxane, poly[1-(trimethylsilyl)-1-propyne], poly(2,6-dimethyl-1,4-phenylene oxide), polyacrylonitrile, polymer of intrinsic microporosity (PIM-1), polystyrene-b-poly(ethylene oxide) diblockcopolymer, poly(sodiumstyrenesulphonate) (PSS) or polyvinylsulphate (PVS) and mixtures thereof; a flowable input of essential oil; wherein the flow rate of the flowable input through the first membrane is at least 8 kg [permeate]/h*m² [membrane]; and wherein the TFC nanofiltration membrane has a molecular weight cut off between 150 g/mol and 1200 g/mol.

* * * * *